US011801103B2

(12) United States Patent
Tojo et al.

(10) Patent No.: US 11,801,103 B2
(45) Date of Patent: Oct. 31, 2023

(54) SURGICAL SYSTEM AND METHOD OF CONTROLLING SURGICAL SYSTEM

(71) Applicants: KAWASAKI JUKOGYO KABUSHIKI KAISHA, Kobe (JP); MEDICAROID CORPORATION, Kobe (JP)

(72) Inventors: Tsuyoshi Tojo, Ibaraki (JP); Kenji Noguchi, Kobe (JP); Tetsushi Ito, Kobe (JP); Tetsuya Nakanishi, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 1220 days.

(21) Appl. No.: 16/396,953

(22) Filed: Apr. 29, 2019

(65) Prior Publication Data

US 2019/0328470 A1 Oct. 31, 2019

(30) Foreign Application Priority Data

Apr. 27, 2018 (JP) ................................. 2018-087501

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/25* (2016.02); *A61B 34/70* (2016.02);
(Continued)

(58) Field of Classification Search
CPC ......... A61B 34/35; A61B 34/25; A61B 34/70; A61B 2034/302; A61B 2034/305;
(Continued)

(56) References Cited

U.S. PATENT DOCUMENTS

2003/0083551 A1 5/2003 Takahashi
2009/0275798 A1 11/2009 Naito
(Continued)

FOREIGN PATENT DOCUMENTS

JP 2000-505328 A 5/2000
JP 2001-512241 A 8/2001
(Continued)

*Primary Examiner* — Aaron F Roane
(74) *Attorney, Agent, or Firm* — Oliff PLC

(57) ABSTRACT

A surgical system includes: a tool manipulator having a tool manipulator arm and a surgical tool; a console having a handling tool configured to receive a tool movement input of a surgeon for the surgical tool, the console being configured to transmit a tool movement command generated based on the tool movement input, the tool movement input including a translation amount and a rotation amount for the surgical tool; and a controller. The controller is configured to calculate an actual translation amount by multiplying the translation amount by a predetermined translation scale factor and move the surgical tool in accordance with the actual translation amount, and to calculate an actual rotation amount by multiplying the rotation amount by a predetermined rotation scale factor and move the surgical tool in accordance with the actual rotation amount. The translation scale factor and the rotation scale factor are different values.

20 Claims, 17 Drawing Sheets

(51) Int. Cl.
    *A61B 17/00*     (2006.01)
    *A61B 34/30*     (2016.01)

(52) U.S. Cl.
    CPC ............... *A61B 2017/00199* (2013.01); *A61B 2017/00207* (2013.01); *A61B 2017/00477* (2013.01); *A61B 2034/302* (2016.02); *A61B 2034/305* (2016.02)

(58) Field of Classification Search
    CPC ........... A61B 2017/00199; A61B 2017/00207; A61B 2017/00477
    USPC ....................................................... 600/114

See application file for complete search history.

(56) References Cited

U.S. PATENT DOCUMENTS

| | | |
|---|---|---|
| 2012/0059392 A1 | 3/2012 | Diolaiti |
| 2016/0199138 A1 | 7/2016 | Cooper et al. |
| 2016/0354164 A1 | 12/2016 | Nichogi et al. |

FOREIGN PATENT DOCUMENTS

| | | |
|---|---|---|
| JP | 2003-222804 A | 8/2003 |
| JP | 2009-268592 A | 11/2009 |
| JP | 2010-259582 A | 11/2010 |
| JP | 2014-57854 A | 4/2014 |
| JP | 2015-502198 A | 1/2015 |
| JP | 2015-159955 A | 9/2015 |
| JP | 2016-530004 A | 9/2016 |
| JP | 2017-514608 A | 6/2017 |
| WO | 97/29690 A1 | 8/1997 |
| WO | 99/06950 A2 | 2/1999 |
| WO | 2013/071057 A1 | 5/2013 |
| WO | 2015/171614 A1 | 11/2015 |
| WO | 2017/075085 A1 | 5/2017 |

SURGICAL SYSTEM AND METHOD OF CONTROLLING SURGICAL SYSTEM

CROSS REFERENCE TO RELATED APPLICATION

This application claims priority to Japanese Patent Application No. 2018-087501, filed with the Japanese Patent Office on Apr. 27, 2018, the entire contents of which are incorporated herein by reference.

BACKGROUND OF THE INVENTION

Field of the Invention

The present invention relates to a surgical system and a method of controlling the surgical system.

Description of Related Art

Conventionally, a surgical system including a master-slave surgical assist robot is known. In surgery using the surgical system, an operator teleoperates movement of the surgical assist robot using a console and the surgical assist robot performs surgery on a patient's surgical site. For example, JP 2016-530004 A discloses this type of surgical system.

The teleoperated surgical system of JP 2016-530004 A is for performing single port laparoscopic surgery. This teleoperated surgical system includes a patient-side cart (corresponding to the surgical assist robot) and a surgeon console. The patient-side cart includes a plurality of surgical device assemblies supported by a manipulator. The surgical device assembly includes an instrument including a surgical tool and a movable wrist, a drive unit for the instrument, and a sterile adapter coupling them.

SUMMARY OF THE INVENTION

For performing laparoscopic surgery, surgical tools are inserted into a patient's abdominal cavity. Convergence of the surgical tools and an endoscope in the abdominal cavity thus causes collision between the surgical tools and narrower working space, which makes it difficult to handle the surgical tools.

The present invention has been made in view of the above circumstances, and an object of the present invention is to assist an operator to handle surgical tools so that collision between the surgical tools is avoided in a surgical system for laparoscopic surgery.

In order to solve the above problems, a surgical system according to an aspect of the present invention includes: a tool manipulator having a tool manipulator arm configured to perform translational motion and rotational motion of a distal end with respect to a proximal end, and a surgical tool linked to the distal end of the tool manipulator arm; a console having a handling tool configured to receive a tool movement command of a surgeon for the surgical tool, the tool movement command including a translation amount of the translational motion and a rotation amount of the rotational motion for the surgical tool; and a controller configured to control the tool manipulator. The controller is configured to calculate an actual translation amount by multiplying the translation amount for the surgical tool received by the handling tool by a predetermined translation scale factor and move the surgical tool in accordance with the actual translation amount, and to calculate an actual rotation amount by multiplying the rotation amount for the surgical tool received by the handling tool by a predetermined rotation scale factor and move the surgical tool in accordance with the actual rotation amount. The translation scale factor and the rotation scale factor are different values.

This configuration enables a surgical tool to move at different scales for different handling such as shift handling and attitude change handling of the surgical tool. This can improve the operability of the surgical system.

The above object, other objects, features, and advantages of the present invention will be apparent from the following detailed description of preferred modes with reference to the attached drawings.

DETAILED DESCRIPTION OF PREFERRED EMBODIMENTS

Figure 1:
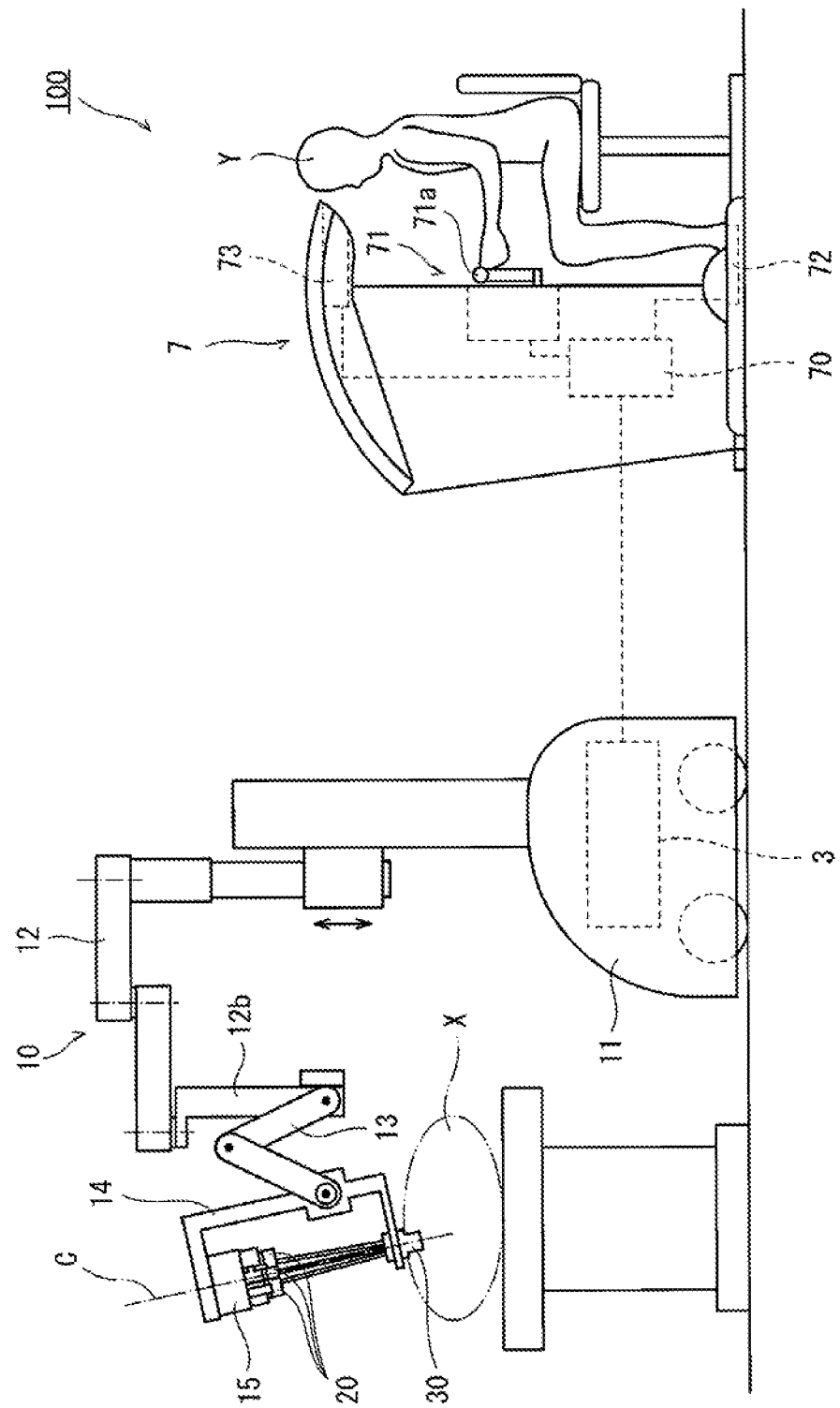
FIG. 1 is a diagram schematically showing an overall configuration example of a surgical system according to a first embodiment.

A surgical system according to an aspect includes: a tool manipulator having a tool manipulator arm configured to perform translational motion and rotational motion of a distal end with respect to a proximal end, and a surgical tool linked to the distal end of the tool manipulator arm; a console having a handling tool configured to receive a tool movement command of a surgeon for the surgical tool, the tool movement command including a translation amount of the translational motion and a rotation amount of the rotational motion for the surgical tool; and a controller configured to control the tool manipulator. The controller is configured to calculate an actual translation amount by multiplying the translation amount for the surgical tool received by the handling tool by a predetermined translation scale factor and move the surgical tool in accordance with the actual translation amount, and to calculate an actual rotation amount by multiplying the rotation amount for the surgical tool received by the handling tool by a predetermined rotation scale factor and move the surgical tool in accordance with the actual rotation amount. The translation scale factor and the rotation scale factor are different values.

This configuration enables a surgical tool to move at different scales for different handling such as shift handling and attitude change handling of the surgical tool. This can improve the operability of the surgical system.

The rotation scale factor may be a value larger than the translation scale factor.

According to this configuration, an operator can easily shift the surgical tool with precision. Meanwhile, the operator can quickly change the attitude of the surgical tool. This can improve the operability of the surgical system.

The surgical system may include an endoscope having a camera probe configured to capture an image of an imaging area surrounded by a boundary including a preset entry restriction boundary. The console may have a display module having a display area on which the image captured by the camera probe is displayed and the display module may be configured to arrange the entry restriction boundary on an upper side of the display area to display the image captured by the camera probe. The controller may be configured to restrict, upon determining that the tool movement command includes a command to move the surgical tool so as to move a restriction target segment set at the distal end side of the tool manipulator into the entry restriction boundary, movement of the surgical tool in a movement direction of the surgical tool that moves the restriction target segment into the entry restriction boundary.

According to this configuration, the extending direction of the tool manipulator in the image displayed on the display module can be maintained equal to the extending direction of the arm of the operator, which can improve the operability of the surgical system.

The endoscope may have an endoscope manipulator arm configured to perform translational motion and rotational motion of a distal end with respect to a proximal end and the camera probe may be linked to the distal end of the endoscope. The handling tool may receive an endoscope manipulator movement command of a surgeon for the camera probe, the endoscope manipulator movement command including a translation amount of the translational motion and a rotation amount of the rotational motion for the camera probe. The controller may be configured to restrict, upon determining that the endoscope manipulator movement command includes a command to move the camera probe so as to move the restriction target segment into the entry restriction boundary, movement of the camera probe in a movement direction of the camera probe that moves the restriction target segment into the entry restriction boundary.

According to this configuration, the extending direction of the tool manipulator in the image displayed on the display module can be maintained equal to the extending direction of the arm of the operator, which can improve the operability of the surgical system.

The surgical system may include an endoscope having an endoscope manipulator arm configured to perform translational motion and rotational motion of a distal end with respect to a proximal end and a camera probe linked to the distal end of the endoscope manipulator arm, and an entry guide having an endoscope insertion hole through which the endoscope manipulator arm is inserted. The console may have a display module having a display area on which an image captured by the camera probe is displayed in a predetermined orientation. The entry guide may have a rotation restriction structure configured to restrict rotation of the endoscope manipulator arm in a circumferential direction around a central axis of the endoscope insertion hole.

According to this configuration, the orientation of the endoscope image with respect to the entry guide and the tool manipulator can be maintained, which allows the operator to easily recognize the position of the surgical tool. This can improve the operability of the surgical system.

The entry guide may have a tool manipulator insertion hole through which the tool manipulator arm is inserted. The tool manipulator arm may be rotatable in a circumferential direction around a central axis of the tool manipulator insertion hole.

According to this configuration, the operability of the surgical system can be further improved.

The surgical system may have an entry guide support structure supporting the entry guide rotatably in a circumferential direction around a central axis of the entry guide.

According to this configuration, the attitude of the distal end of the surgical assist robot can change with the orientation of the endoscope image with respect to the entry guide and the tool manipulator maintained. This can improve the operability of the surgical system.

The surgical system may include an endoscope having an endoscope manipulator arm configured to perform translational motion and rotational motion of a distal end with respect to a proximal end and a camera probe linked to the distal end of the endoscope manipulator arm, and an entry guide having an insertion hole through which the tool manipulator arm and the endoscope manipulator arm are inserted. The controller may be configured to shift the tool manipulator arm in an extending direction of the insertion hole with respect to the entry guide within a predetermined first movement range, and shift the endoscope manipulator arm in the extending direction of the insertion hole with respect to the entry guide within a predetermined second movement range. A distal-end-side limit of the second movement range may be located more proximally than a distal-end-side limit of the first movement range.

According to this configuration, it is possible to effectively prevent losing sight of the surgical tool which has gone out of view of the camera probe. This can improve the operability of the surgical system.

The surgical system may have an entry guide having an insertion hole through which the tool manipulator arm and the surgical tool are inserted. The tool manipulator arm may have a wrist structure that is provided at a proximal side of the surgical tool and performs at least a part of the translational motion and the rotational motion of the tool manipulator arm. The tool manipulator may have a brake configured to restrict movement of the wrist structure by actuation and allow the movement of the wrist structure by deactuation. The controller may be configured to actuate the brake when the wrist structure is located more proximally than a distal end of the entry guide or on the distal end of the entry guide in an extending direction of the tool manipulator arm.

According to this configuration, the tool manipulator can be rapidly introduced into the body cavity of the patient, which can improve the operability of the surgical system.

The surgical system may have an entry guide having a tool manipulator insertion hole through which the tool manipulator arm and the surgical tool are inserted. The tool manipulator arm may have a wrist structure that is provided at a proximal side of the surgical tool and performs at least a part of the translational motion and the rotational motion of the tool manipulator arm by movement of the wrist structure. The controller may be configured to invalidate a movement command for the wrist structure included in the tool movement command when the wrist structure is located more proximally than a distal end of the entry guide or on the distal end of the entry guide in an extending direction of the tool manipulator arm.

According to this configuration, the tool manipulator can be rapidly introduced into the body cavity of the patient, which can improve the operability of the surgical system.

The surgical system may include an endoscope having a body wall geometry sensing section configured to derive information for detecting geometry of a body wall forming a body cavity of a patient and a notification section configured to notify the surgeon of information. The controller may be configured to calculate the geometry of the body wall based on the information derived by the body wall geometry sensing part, set an entry forbidden area based on the calculated geometry of the body wall, and repeatedly determine whether the tool manipulator has entered the entry forbidden area and control, upon determining that the tool manipulator has entered the entry forbidden area, the notification section to notify the surgeon of the entry of the tool manipulator to the entry forbidden area.

According to this configuration, collision between the tool manipulator and the body wall can be prevented, which can improve the operability of the surgical system.

The body wall geometry sensing section may be a pair of camera probes provided at a distal end of the endoscope and arranged with predetermined spacing. The controller may be configured to dispersedly set a plurality of interest points on the body wall recorded in images captured by the pair of camera probes, calculate, for each of the interest points, coordinates of the interest point with respect to a predetermined reference point, based on a relative positional relationship between a position of the interest point in a first image captured by one of the camera probes and a position of the interest point in a second image captured by the other of the camera probes simultaneously with the first image, and calculate the geometry of the body wall based on the calculated three-dimensional coordinates of the plurality of interest points.

According to this configuration, the geometry of the body wall can be appropriately calculated using the endoscope.

The endoscope may include a laser pointer provided at the distal end of the endoscope and configured to emit a laser beam. The controller may be configured to set irradiation portions of the laser beam recorded in the first image and the second image as the interest points in the first image and the second image, respectively.

According to this configuration, the geometry of the body wall can be easily calculated.

The controller may be configured to set the interest point in the first image in which the body wall is recorded and calculate a place in the second image in which the body wall is recorded to set the interest point in the second image, the place being identical to a place of the interest point in the first image and calculated by pattern matching between the first image and the second image.

According to this configuration, the geometry of the body wall can be easily calculated with the simple configuration.

The surgical system may include an endoscope having a pair of camera probes arranged with predetermined spacing and a notification section configured to notify the surgeon of information. The controller may be configured to set an interest point on a body wall forming a body cavity of a patient recorded in images captured by the camera probes, calculate an initial position that is a position of the pair of camera probes with respect to the interest point, based on a relative positional relationship between a position of the interest point in a first image captured by one of the camera probes and a position of the interest point in a second image captured by the other of the camera probes, repeatedly calculate a present position that is a position of the camera probes with respect to the interest point, based on the relative positional relationship between the position of the interest point in the first image and the position of the interest point in the second image, determine whether the present position has changed by a predetermined threshold or more with respect to the initial position, and control, upon determining that the present position has changed by the predetermined threshold or more with respect to the initial position, the notification section to notify the change in the present position.

According to this configuration, the operator can recognize that the position of the camera probes has changed due to unexpected change of the position of the entry guide. This can improve the operability of the surgical system.

The endoscope may have an endoscope manipulator arm configured to perform translational motion and rotational motion of a distal end with respect to a proximal end and the pair of camera probes may be linked to the distal end of the endoscope. The controller may be configured to move the pair of camera probes toward the initial position upon determining that the present position has changed by a predetermined threshold or more with respect to the initial position.

According to this configuration, the camera probes automatically return to the initial position even when the position of the camera probes has changed due to unexpected change of the position of the entry guide, which can alleviate adverse effect on the operability for the operator and improve the operability of the surgical system.

A method of controlling a surgical system according to an aspect, the surgical system including a tool manipulator having a tool manipulator arm configured to perform translational motion and rotational motion of a distal end with respect to a proximal end and a surgical tool linked to the distal end of the tool manipulator arm, a console having a handling tool configured to receive a tool movement command of a surgeon for the surgical tool, the tool movement command including a translation amount of the translational motion and a rotation amount of the rotational motion for the surgical tool, and a controller configured to control the tool manipulator, has calculating, by the controller, an actual translation amount by multiplying the translation amount for the surgical tool received by the handling tool by a predetermined translation scale factor, moving, by the controller, the surgical tool in accordance with the actual translation amount, calculating, by the controller, an actual rotation amount by multiplying the rotation amount for the surgical tool received by the handling tool by a predetermined rotation scale factor that is a value different from the translation scale factor, and moving, by the controller, the surgical tool in accordance with the actual rotation amount.

This configuration enables a surgical tool to move at different scales for different handling such as shift handling and attitude change handling of the surgical tool. This can improve the operability of the surgical system.

Next, embodiments will be described with reference to the drawings. Note that the following embodiments do not limit the present invention. Hereinafter, the same or corresponding elements will be denoted by the same reference symbols throughout all the drawings and overlapping description will be omitted.

First Embodiment

Figure 2:
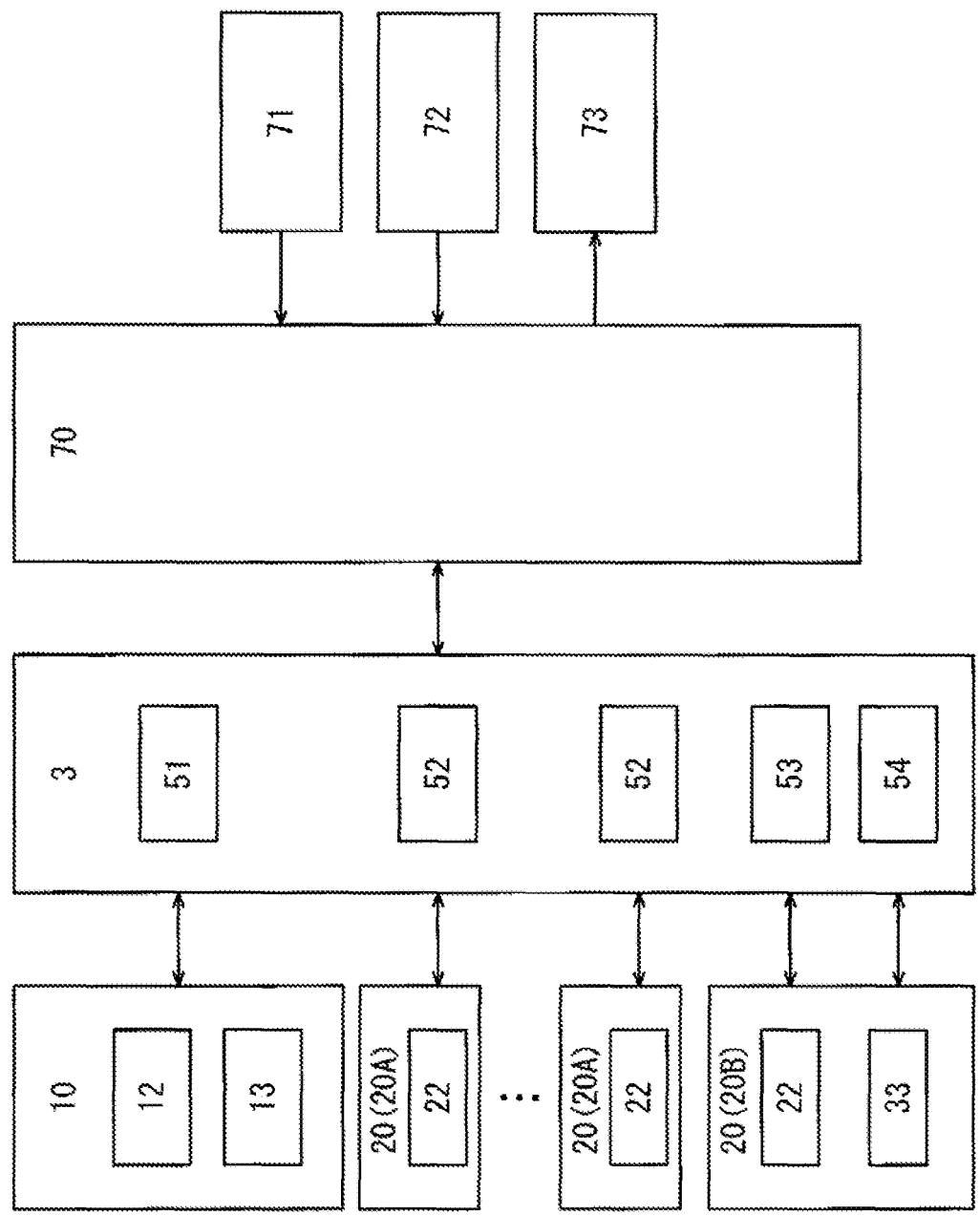
FIG. 2 is a block diagram schematically showing a configuration example of a control system of the surgical system of FIG. 1.

FIG. 1 is a diagram schematically showing an overall configuration example of a surgical system 100 according to a first embodiment. FIG. 2 is a block diagram schematically showing a configuration example of a control system of the surgical system 100. The surgical system 100 shown in FIGS. 1 and 2 is for performing single port laparoscopic surgery and includes a surgical assist robot 1, a console 7, and a controller 3 for controlling the surgical system 100. Hereinafter, each component of the surgical system 100 will be described in detail.

[Surgical Assist Robot 1]

The surgical assist robot 1 constitutes an interface between the surgical system 100 and a patient X. The surgical assist robot 1 is placed beside a surgical table on which the patient X lies in a surgery room which is a sterile field.

The surgical assist robot 1 includes a plurality of surgical assemblies 20, an entry guide 30, and a positioner 10 that positions the surgical assemblies 20 and the entry guide 30 with respect to the patient X. The positioner 10 positions the entry guide 30 coaxially with a predetermined central axis C extending in a direction toward a surgical target site in the body cavity (abdominal cavity) of the patient X and supports the plurality of surgical assemblies 20 inserted in the entry guide 30.

The entry guide 30, which is a rigid tube (see FIG. 5) and is attached to a cannula (not shown) placed on the patient's body surface, has insertion holes through which the respective surgical assemblies 20 are inserted, i.e., two tool manipulator insertion holes 30A and one endoscope insertion hole 30B. The central axis of each insertion hole extends parallel to the central axis C. The insertion hole holds the central axis of the corresponding surgical assembly 20 inserted therethrough coaxially with the central axis of the insertion hole and guides the surgical assembly 20 in the extending direction of the insertion hole, i.e., the extending direction of the central axis C. The inner periphery of each insertion hole is formed to have a circular cross section, which allows the surgical assembly 20 to rotate in the circumferential direction around the central axis of the insertion hole. Further, each insertion hole has a diameter through which a shaft 26, a wrist 27, and an end effector such as a surgical tool 28 or an endoscopic camera unit 33 linked to the wrist 27 can be inserted. Note that the tool manipulator insertion holes 30A and the endoscope insertion hole 30B may be one insertion hole of which central axis coincides with the central axis C.

The positioner 10 serves as a supporter that supports and guides the surgical assemblies 20 and the entry guide 30. The positioner 10 includes a horizontal articulated manipulator 12 supported by a wagon 11, a support member 12b provided at the distal end part of the horizontal articulated manipulator 12, a vertical articulated manipulator 13 supported by the horizontal articulated manipulator 12 via this support member 12b, and a support frame 14 provided at the distal end part of the vertical articulated manipulator 13. Changing the attitudes of the horizontal articulated manipulator 12 and the vertical articulated manipulator 13 allows the support frame 14 to change attitude in the circumferential direction around the central axis C. However, the configuration of the positioner 10 is not limited to this embodiment, and may be any configuration that allows the entry guide 30 to be positioned at a target position (and in a target attitude) with sufficient accuracy. The horizontal articulated manipulator 12 and the vertical articulated manipulator 13 of the positioner 10 are provided for each joint with a drive section including a servomotor and a power transmission mechanism for transmitting power of the servomotor to the joint (both of them not shown).

The support frame 14 is channel-shaped. One end part of the support frame 14 faces to the other end part with a space in the extending direction of the central axis C. One end part of the support frame 14 is provided with an entry guide support section 14b supporting the entry guide 30. The other end part of the support frame 14 is provided with a surgical device support section 14a.

Figure 3:
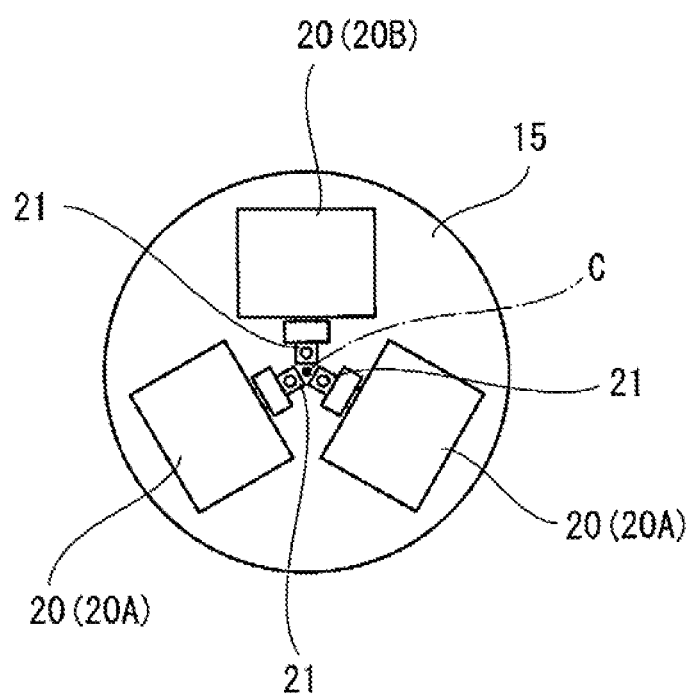
FIG. 3 is a diagram showing a placement configuration of surgical assemblies on a support block of the surgical system of FIG. 1.

FIG. 3 is a diagram showing a placement configuration of the surgical assemblies 20 on a support block 15 of the surgical system 100, where the support block 15 is viewed from the extending direction of the central axis C.

The surgical device support section 14a is provided with the support block 15 that collectively supports the plurality of surgical assemblies 20. In the present embodiment, the plurality of surgical assemblies 20 include two surgical assemblies 20A each having the surgical tool 28 and one surgical assembly 20B having the endoscopic camera unit 33. These three surgical assemblies 20 are arranged circumferentially around the central axis C as shown in FIG. 3.

Change in the attitude of the support frame 14 in the circumferential direction around the central axis C is accompanied with changes in the attitudes of tool manipulators 21 supported by the entry guide 30 and the surgical device support section 14a in the circumferential direction around the central axis C. The positioner 10 is an entry guide support structure that supports the entry guide 30 rotatably in the circumferential direction around the central axis of the entry guide 30.

It should be noted that the terms "proximal" or "proximally" are used to describe, in a general way, an object or an element closer to the positioner 10 along the kinematic chain of the system motion or further away from the remote center of motion (or surgical site) along the kinematic chain of the system motion. Similarly, the terms "distal" or "distally" are used to describe, in a general way, an object or an element further away from the positioner 10 along the kinematic chain of the system motion or closer to the remote center of motion (or surgical site) along the kinematic chain of the system motion.

(Surgical Assembly 20A)

Figure 4:
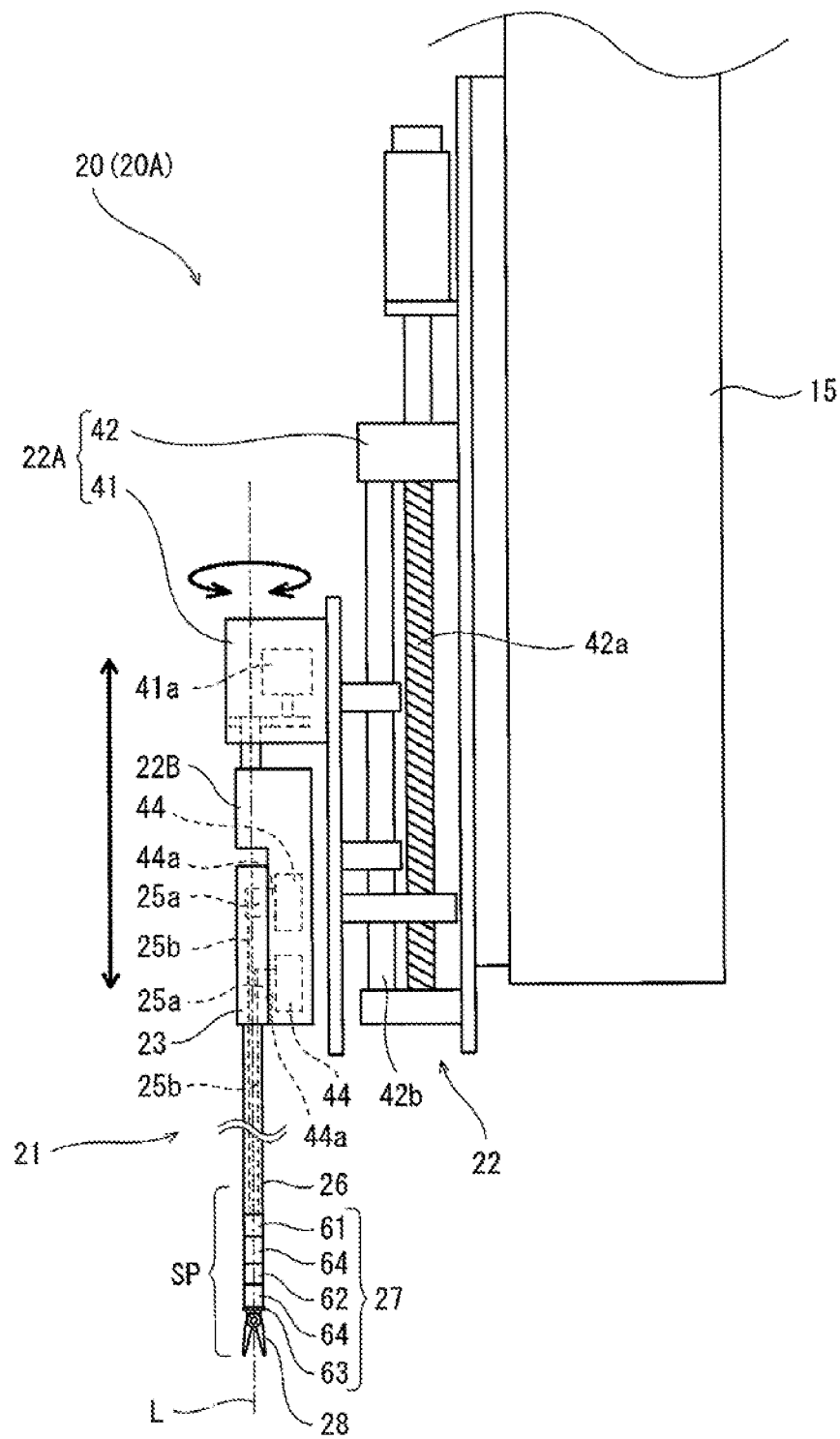
FIG. 4 is a side view showing a configuration example of the surgical assembly having a surgical tool of the surgical system of FIG. 1.
Figure 5:
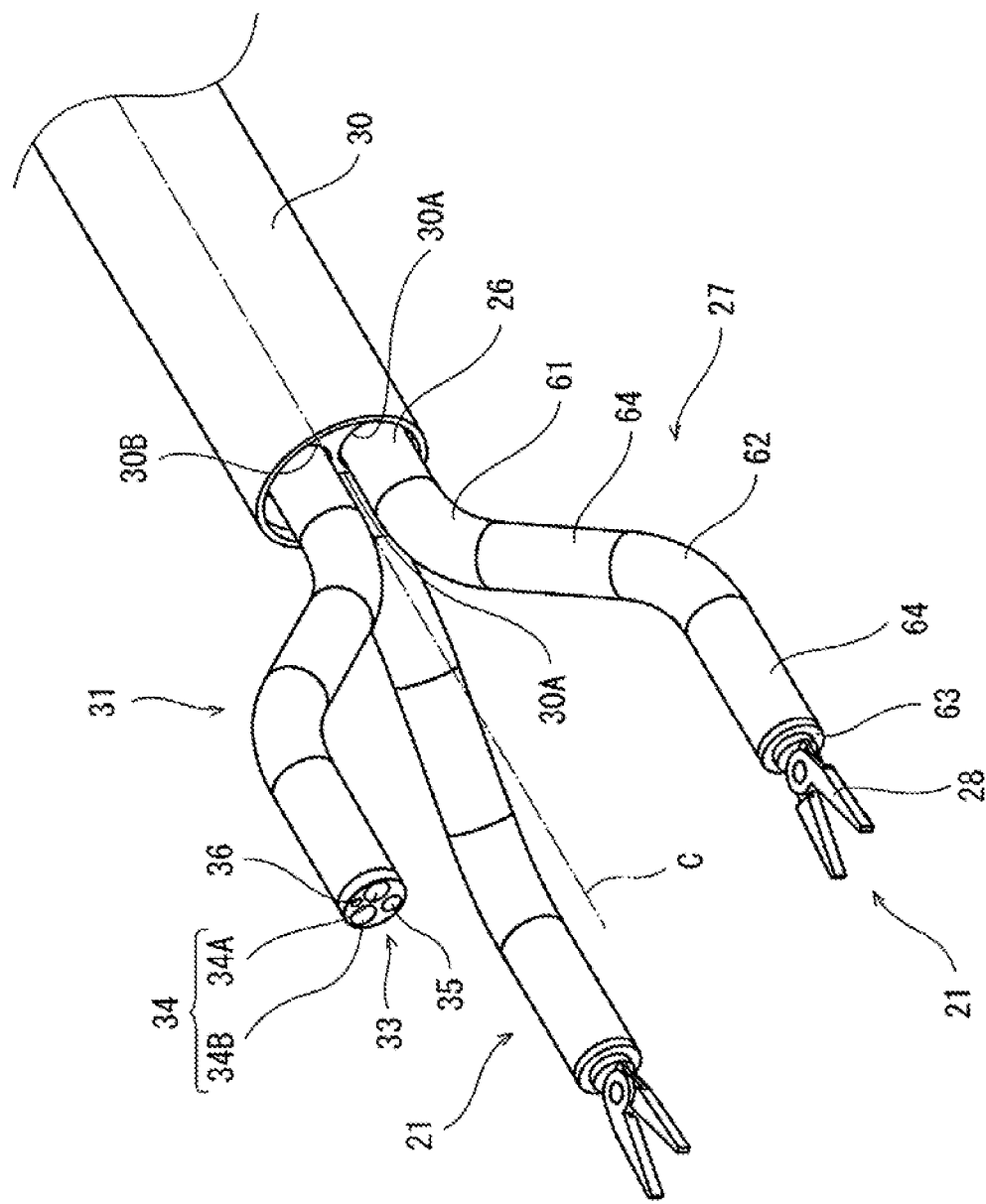
FIG. 5 is a perspective view showing a configuration example of a distal end of a surgical assist robot of the surgical system of FIG. 1.

FIG. 4 is a side view showing an example of the surgical assembly 20A having the surgical tool 28 of the surgical system 100. FIG. 5 is a perspective view showing a distal end of the surgical assist robot 1 of the surgical system 100.

The surgical assembly 20A shown in FIG. 4 includes the tool manipulator 21 provided with the surgical tool 28 at its distal end and a drive unit 22 that is coupled to the tool manipulator 21 and drives the tool manipulator 21.

The tool manipulator 21 has a base 23, the elongated hollow shaft 26, the wrist 27, and the surgical tool 28 as an end effector and they are linked in this order from proximal to distal. It should be noted that "linked" includes not only the case where two things are directly connected to each other but also the case where two things are indirectly connected to each other with another thing interposed between them. The base 23, the shaft 26, the wrist 27, and the surgical tool 28 are integrally configured.

The base 23 is a connector removably connected to a second sub drive unit 22B described later and is a housing that accommodates therein a transmission unit such as a driven pulley 25a and a transmission wire 25b described later.

The shaft 26 is configured with a rigid tube of which proximal end is attached to the base 23 and of which central axis L extends in a straight line. As shown in FIG. 5, the shaft 26 is inserted through the tool manipulator insertion hole 30A and is movable in the extending direction of this insertion hole with respect to the tool manipulator insertion hole 30A. The shaft 26 has an outer periphery that is formed to have a circular cross section and is rotatable in the circumferential direction around the central axis of the tool manipulator insertion hole 30A, i.e., the central axis L of the shaft 26, with respect to the tool manipulator insertion hole 30A. Note that the central axis of the tool manipulator insertion hole 30A is located eccentrically from the central axis of the entry guide 30 and thus rotation of the entry guide 30 in the circumferential direction around the central axis C is accompanied by rotation of the surgical assembly 20A in the circumferential direction around the central axis C. The internal space of the shaft 26 is connected to the internal space of the base 23 on the proximal side and is connected to the wrist 27 on the distal side. The transmission wire 25b described later extending from the base 23 toward the wrist 27 is located in the internal space of the shaft 26.

As shown in FIGS. 4 and 5, the proximal end of the wrist (wrist structure) 27 is linked to the distal end of the shaft 26. The wrist 27 includes, for example, a proximal bending joint 61 and a distal bending joint 62 that perform bending movement in a radial direction of the central axis L, and a wrist joint 63 that performs twisting movement in the circumferential direction around the central axis L. The wrist 27 performs at least a part of translational motion and rotational motion of the surgical assembly 20A described later. The proximal bending joint 61, the distal bending joint 62, and the wrist joint 63 are linked in this order from proximal to distal. Adjacent joints are also coupled by a coupling section 64. The proximal bending joint 61, the distal bending joint 62, and the wrist joint 63 are actuated by traction force and/or tension of the transmission wire 25b described later.

The surgical tool 28, which is linked to the wrist joint 63, is a pair of forceps, for example. The forceps are opened and closed by traction force and/or tension of the transmission wire 25b described later. Note that the surgical tool 28 performs bending movement in a radial direction of the central axis L by its movement. The surgical tool 28 may be a surgery tool such as a pair of forceps, a grasper, a pair of scissors, a stapler, a needle holder, or an electric scalpel. The surgical tool 28 may also be an electrically driven instrument such as an electrosurgical electrode, a transducer, or a sensor. The surgical tool 28 may also be a nozzle that supplies fluid for suction, gas injection, washing, treatment fluid, accessory introduction, excisional biopsy, or the like.

The tool manipulator 21 further has a transmission unit that transmits the driving force of the drive unit 22. The transmission unit has the driven pulley 25a provided at the base 23. For example, a plurality of driven pulleys 25a are provided corresponding to the actuation sections of the wrist 27 and the surgical tool 28. Each driven pulley 25a and a corresponding drive pulley 44a described later are connected so as to engage and disengage. Engagement of both pulleys causes the driven pulley 25a to follow the rotation of the drive pulley 44a, resulting in transmission of the driving force of the drive pulley 44a to the driven pulley 25a. As described above, the configuration of the tool manipulator 21 that is detachable from the drive unit 22 allows easy sterilization and replacement of the tool manipulator 21. The driven pulley 25a, to which the transmission wire 25b is attached, is configured to rotate to apply traction force and/or tension to the transmission wire 25b. This transmission wire 25b extends through the shaft 26 to a corresponding one of the joints of the wrist 27 and the surgical tool 28 that, connects the driven pulley 25a and the element corresponding to this driven pulley 25a, and transmits the traction force of the transmission wire 25b to this corresponding element. Such mechanisms are described in WO 2017/006376 A, which is incorporated herein by reference, for example. However, the present invention is not limited to the above configuration and a known mechanism may be used.

The drive unit 22, which shifts the surgical tool 28 and changes the attitude of the surgical tool 28, includes a first sub drive unit 22A and the second sub drive unit 22B. Note that, hereinafter, shifting the surgical tool 28 and changing the attitude of the surgical tool 28 may be simply described as moving the surgical tool 28.

The first sub drive unit 22A rotates the tool manipulator 21 in the circumferential direction around the central axis L of the shaft 26 and translates the tool manipulator 21 in the extending direction of the central axis L. The first sub drive unit 22A has a rotation driver assembly 41 and a translation driver assembly 42 as shown in FIG. 4.

The rotation driver assembly 41 is a mechanism that integrally supports and drives the tool manipulator 21 and the second sub drive unit 22B rotatably in the circumferential direction around the central axis L. The rotation driver assembly 41 has an actuator 41a such as a servomotor. The output axis of the actuator 41a is linked via a gear train to the second sub drive unit 22B rotatably around the central axis L. Accordingly, the driving force of the actuator 41a rotates the tool manipulator 21 and the second sub drive unit 22B in the circumferential direction around the central axis L with respect to the drive unit 22.

The translation driver assembly 42, which is attached to the support block 15, is a mechanism that integrally supports and drives the tool manipulator 21, the second sub drive unit 22B, and the rotation driver assembly 41 translatably in the extending direction of the central axis L. The translation driver assembly 42 has a ball screw mechanism 42a having an actuator such as a servomotor and a linear guide 42b that guides the rotation driver assembly 41 in the extending direction of the central axis L. The driving force of the ball screw mechanism 42a shifts the tool manipulator 21 in the extending direction of the central axis L with respect to the drive unit 22. The translation driver assembly 42 is linked to the proximal side of the rotation driver assembly 41, but not limited to this. Alternatively, the translation driver assembly 42 may be linked to the distal side of the rotation driver assembly 41.

The second sub drive unit 22B is linked to the distal side of the first sub drive unit 22A and is interposed between the first sub drive unit 22A and the tool manipulator 21. The second sub drive unit 22B moves the wrist 27 and the surgical tool 28 by its driving force. In the present embodiment, the second sub drive unit 22B has actuators 44 such as servomotors provided corresponding to the movement portions of the respective joints of the wrist 27 and the surgical tool 28. The output axis of each actuator 44 is coupled to the drive pulley 44a provided correspondingly.

In this manner, a combination of translational motion and rotational motion of the entire tool manipulator 21, motion of the joints of the wrist 27, and movement of the surgical tool 28 realizes translational motion of the surgical tool 28 in respective axial directions of the X, Y, and Z axes and rotational motion of the surgical tool 28 in respective circumferential directions around the X, Y, and Z axes in a predefined surgical-assist-robot-side three-dimensional orthogonal coordinate system. Thus, the surgical assembly 20A makes the surgical tool 28 perform translational motion and rotational motion with respect to a predetermined reference point. A tool manipulator arm has a configuration for realizing the translational motion and rotational motion, and in the present embodiment, includes the drive unit 22, the base 23, the shaft 26, the wrist 27, the surgical tool 28, and the transmission unit. As described above, the surgical assembly 20A has six independent drive joints of the mechanism that translates and rotates the overall tool manipulator 21 and bends the three joints of the wrist 27 and the surgical tool 28. That is, the surgical assembly 20A is a manipulator that moves in six degrees of freedom but may move in more degrees of freedom. Note that a configuration for realizing the translational motion and rotational motion of the surgical assembly 20A is not limited to the above configuration.

(Surgical Assembly 20B)

Figure 6:
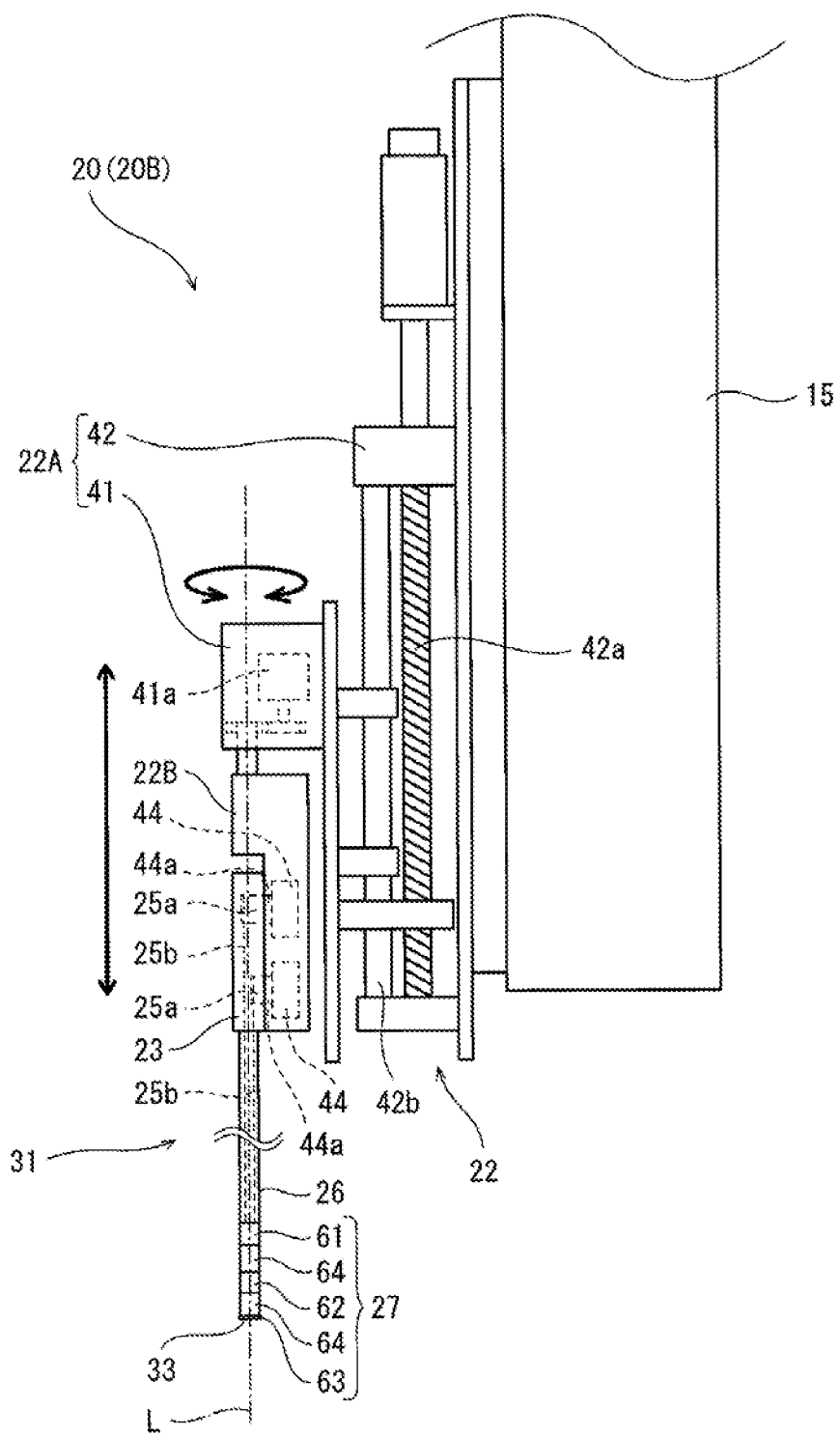
FIG. 6 is a side view showing a configuration example of the surgical assembly having an endoscopic camera of the surgical system of FIG. 1.
Figure 7:
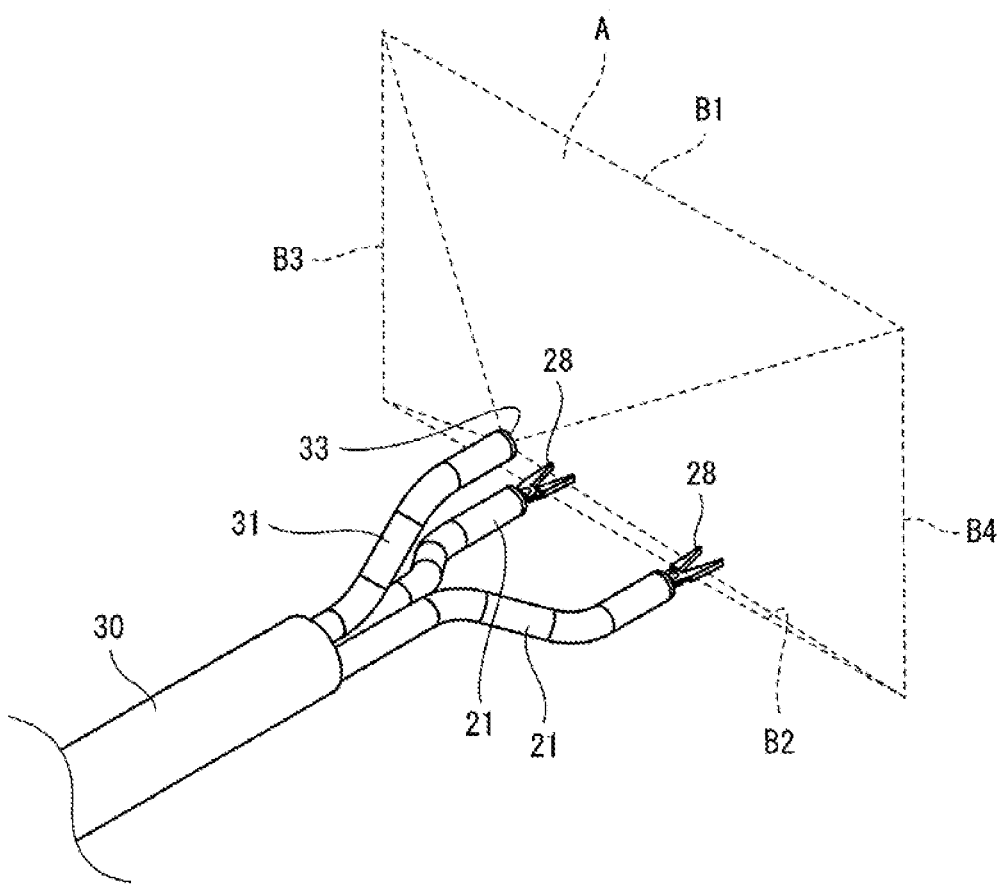
FIG. 7 is a diagram illustrating a relationship between camera probes and an imaging area of the surgical system of FIG. 1.

FIG. 6 is a side view showing a configuration example of the surgical assembly 20B having the endoscopic camera unit 33. FIG. 7 is a diagram illustrating a relationship between camera probes 34 (see FIG. 5) and an imaging area A.

As shown in FIGS. 5 and 6, the surgical assembly 20B includes an endoscope manipulator 31 and the drive unit 22 that is coupled to the endoscope manipulator 31 and drives the endoscope manipulator 31. The endoscope manipulator 31 is inserted through the endoscope insertion hole 30B of the entry guide 30.

The endoscope manipulator 31 is provided with the endoscopic camera unit 33 at its distal end. The endoscope manipulator 31 has substantially the same configuration as the tool manipulator 21 except for the surgical tool 28 provided at the distal end part. That is, the above description of the tool manipulator 21 can explain the configuration of the endoscope manipulator 31 by replacing the surgical tool 28 provided at the distal end part with the endoscopic camera unit 33. Further, the drive unit has substantially the same configuration as the drive unit 22. Accordingly, detailed description of the configuration of the surgical assembly 20B, except for the endoscopic camera unit 33, is omitted by referring to the above description of the surgical assembly 20A. It should be noted that, in the surgical assembly 20B, the tool manipulator arm is referred to as an endoscope manipulator arm in order to avoid confusion of the terms.

The endoscopic camera unit 33 has a pair of camera probes 34 (34A and 34B) which are stereo video cameras, a light 35, and a laser pointer 36. The laser pointer 36 can emit a laser beam to any point within a predetermined range in front.

As shown in FIG. 7, each camera probe 34 captures an image of an imaging area A surrounded by boundaries B1 to B4 and acquires the image data. The pair of camera probes 34 are arranged in the lateral direction of this image. Of the pair of camera probes 34, the camera probe 34A at the left side of the image is associated with a left display section 73A described later, and the camera probe 34B at the right side of the image is associated with a right display section 73B described later.

[Console 7]

As shown in FIG. 1, the console 7 constitutes an interface between the surgical system 100 and the operator (surgeon) Y and is an apparatus for handling the surgical assist robot 1. The console 7 is installed beside or away from the surgical table in the surgery room, or outside the surgery room.

The console 7 includes handling tools for receiving input of a movement command from the operator Y including a handling manipulator arm 71 and a plurality of handling pedals 72, and a display module 73 that displays an image captured by the endoscopic camera unit 33. The handling manipulator arm 71 is provided at its leading end with a handling rod 71a that the operator Y grasps in entering a movement command. A base end of the handling manipulator arm 71 is supported by the console 7. A plurality of joints (not shown) are linked from the handling rod 71a toward the base end. Movements of the plurality of joint enable the handling rod 71a to shift within a three-dimensional movement area and to change its attitude. That is, the handling rod 71a has three translational degrees of freedom and three rotational degrees of freedom. Each joint is provided with a sensor that senses movement of the joint resulted from shifting movement or attitude change movement of the handling rod 71a. The controller 3 calculates the position and the attitude of the handling rod 71a by combining the movements of the joints sensed by the sensors of the respective joints. Then, a handling target selection pedal (not shown) included in the handling pedals 72 selects and decides whether a movement command input to the handling rod 71a is a tool movement command which is a movement command for the surgical assemblies 20A, or an endoscope movement command which is a movement command for the surgical assembly 20B.

Figure 8:
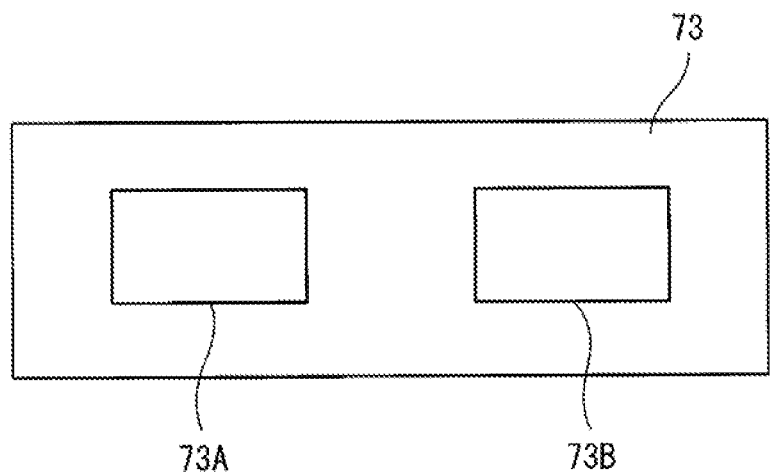
FIG. 8 is a diagram showing a configuration example of a display module of the surgical system of FIG. 1.

FIG. 8 is a diagram showing a configuration example of the display module 73.

As shown in FIGS. 1 and 8, the display module 73 has a pair of left and right display sections (display areas) 73A and 73B respectively corresponding to the eyes of the operator Y. The left display section 73A displays an image captured by one of the pair of camera probes 34 and the right display section 73B displays an image captured by the other of the camera probes 34. The boundaries B1 to B4 (see FIG. 7) of the image are displayed so as to be located on the upper, lower, left, and right boundaries of the display section, respectively. This allows the operator Y to stereoscopically view the inside of the body cavity of the patient X. The operator Y handles the handling tool while stereoscopically viewing the affected part with the display module 73 and thus inputs a tool movement command to move the surgical tools 28 and an endoscope movement command to move the endoscopic camera unit 33.

The console 7 also has a console controller 70 that receives a movement command (a tool movement command and an endoscope movement command) input by the handling tool and transmits the movement command to the controller 3.

Furthermore, the display module 73 displays a text and an icon in a superimposed manner on an image displayed on the display section. This means that the display module 73 also serves as a notification section that notifies the operator Y of information.

[Controller 3]

As shown in FIG. 2, the controller 3 communicably connects to the console controller 70. The controller 3 moves the surgical assemblies 20 in response to a movement command received via the console controller 70.

The controller 3 is a so-called computer and has an arithmetic processing unit such as a CPU and a storage unit such as a ROM and a RAM (all not shown). The storage unit stores programs executed by the arithmetic processing unit, various fixed data, and the like. The various fixed data includes a translation scale factor, a rotation scale factor, an entry restriction boundary BP, a first restriction target segment P1, a second restriction target segment P2, an operable range of the tool manipulator 21 including a first penetration limit position L1, and an operable range of the endoscope manipulator 31 including a second penetration limit position L2 described later. The arithmetic processing unit transmits/receives data to/from other apparatuses including the console 7. The arithmetic processing unit also performs input of detection signals from various sensors and output of control signals to each control target. The arithmetic processing unit reads and executes software such as programs stored in the storage unit, which causes the controller 3 to perform processes for realizing a function as the controller 3 described later. Note that the controller 3 may execute each process under centralized control by a single computer or under distributed control by cooperation of a plurality of computers. The controller 3 may be configured with a microcontroller, a programmable logic controller (PLC), or the like. The controller 3 includes a positioner control section 51, a tool control section 52, an endoscope control section 53, and a display control section 54. The positioner control section 51, the tool control section 52, the endoscope control section 53, and the display control section 54 are functional blocks realized by the arithmetic processing unit executing predetermined control programs stored in the storage unit.

The positioner control section 51, the tool control section 52, and the endoscope control section 53 include a servo control section (not shown) connected to the servomotors via amplification circuits or the like. The positioner control section 51 controls the drive section of each joint based on the rotational position detected by a rotation sensor attached to each servomotor so that the entry guide 30 is positioned at a predetermined position and in a predetermined attitude. The tool control section 52 controls the drive sections of the drive units 22 based on the rotational position detected by a rotation sensor attached to each servomotor so that the surgical assemblies 20A move in accordance with a tool movement command. The tool control section 52 also controls movements of the surgical tools 28. The endoscope control section 53 controls the drive section of the drive unit 22 based on the rotational position detected by a rotation sensor attached to each servomotor so that the surgical assembly 20B moves in accordance with an endoscope movement command. The endoscope control section 53 also controls the movement of the endoscopic camera unit 33. The display control section 54 processes images captured by the camera probes 34 to display the processed images on the display module 73.

Based on the movement of the handling rod 71a sensed by a sensing section of the handling manipulator arm 71, the controller 3 calculates changes in the position and the attitude of the handling rod 71a in a console-side three-dimensional orthogonal coordinate system, i.e., a translation amount of translational motion of the handling rod 71a in respective axial directions of the X, Y, and Z axes and a rotation amount of rotational motion of the handling rod 71a in at least one of circumferential directions around the X, Y, and Z axes in the console-side three-dimensional orthogonal coordinate system. When the surgical assemblies 20A are selected by the handling target selection pedal, the controller 3 treats the translation amount and the rotation amount as a tool movement command. When the surgical assembly 20B is selected by the handling target selection pedal, the controller 3 treats the translation amount and the rotation amount as an endoscope movement command. The controller 3 then converts the changes in the position and the attitude of the handling rod 71a in the console-side three-dimensional orthogonal coordinate system to changes in the position and the attitude of the handling target (i.e., the surgical tool 28 or the endoscopic camera unit 33) in the surgical-assist-robot-side three-dimensional orthogonal coordinate system. The controller 3 associates the converted changes with the handling target. The tool control section 52 and the endoscope control section 53 respectively control movements of the surgical assemblies 20A and the surgical assembly 20B so as to change the position and the attitude of the handling target in accordance with the changes in the position and the attitude of the handling rod 71a. That is, the controller 3 translates and rotates the handling target so that the handling target moves in accordance with the translation amount of the translational motion and the rotation amount of the rotational motion of the handling rod 71a.

[Movement Example of the Surgical System 100]

First, the controller 3 moves the positioner 10 so as to position the entry guide 30 at a predetermined position and in a predetermined attitude with respect to the cannula placed on the body surface of the patient X in response to a positioning command for the entry guide 30 received by the console 7. When the entry guide 30 is positioned, the plurality of surgical assemblies 20 are followingly positioned.

The controller 3 also moves the translation driver assemblies 42 of the drive units 22 so as to insert the endoscopic camera unit 33 and the surgical tools 28 into the body cavity of the patient X in response to a movement command received by the console 7, for example.

Here, the controller 3 moves the tool manipulators 21 and the endoscope manipulator 31 by adding various modifications to the tool movement command and the endoscope movement command input by the operator Y. These modification processes will be described in detail below.

(Scale Change Process)

The controller 3 performs a scale change process for adjusting the movement amount of the tool movement command of the operator Y to move the tool manipulators 21 and the endoscope manipulator 31.

Figure 9:
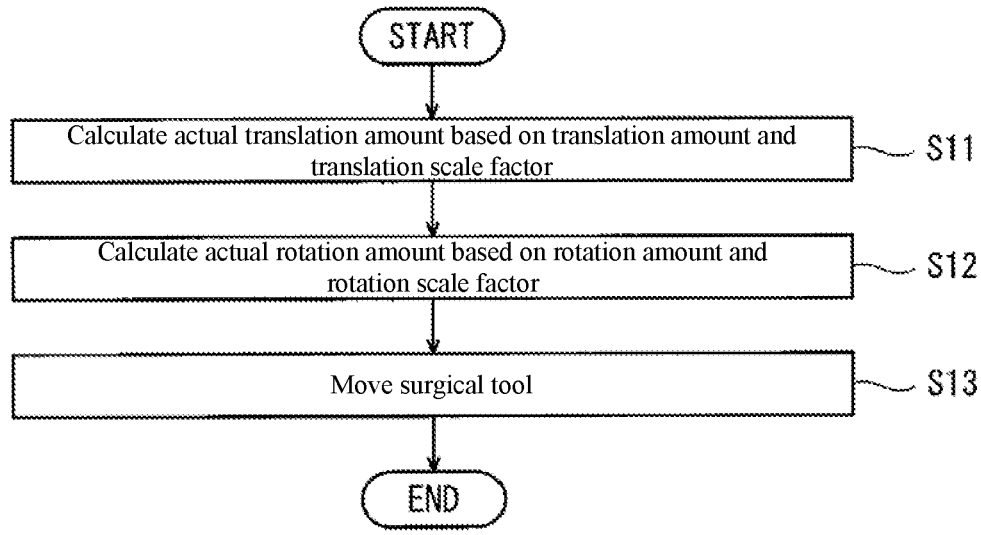
FIG. 9 is a flow chart showing an example of a scale change process of the surgical system of FIG. 1.

FIG. 9 is a flow chart showing an example of the scale change process of the surgical system 100.

First, as shown in FIG. 9, the controller 3 calculates an actual translation amount of the surgical tool 28 in a state where the surgical assembly 20A is selected by the handling target selection pedal (step S11). The calculation is performed by multiplying the translation amounts of the handling rod 71a in respective axial directions of the X, Y, and Z axes in the console-side three-dimensional orthogonal coordinate system sensed by the sensing section of the handling manipulator arm 71 by a predetermined translation scale factor. The translation scale factor is a value less than 1 so that the output is smaller than the input.

The controller 3 also calculates the actual rotation amount of the surgical tool 28 by multiplying the rotation amounts of the handling rod 71a in respective circumferential directions around the X, Y, and Z axes in the console-side three-dimensional orthogonal coordinate system sensed by the sensing section of the handling manipulator arm 71 by a predetermined rotation scale factor (step S12). The rotation scale factor is a value of 1 or more so that the output is equal to or larger than the input. Accordingly, the rotation scale factor is set to a value larger than the translation scale factor.

The controller 3 then decides movement contents of the drive unit 22 so that the surgical tool 28 takes a target attitude resulted from shifting by the actual rotation amount at a target position resulted from translating by the actual translation amount in the surgical-assist-robot-side three-dimensional orthogonal coordinate system corresponding to the console-side three-dimensional orthogonal coordinate system. The controller 3 moves the surgical tool 28 in accordance with the decided movement contents (step S13).

The controller 3 thus calculates the actual translation amount of the actual surgical tool 28 by multiplying the translation amount input by the operator Y by the scale factor less than 1, which causes the surgical tool 28 to move by a reduced movement amount of the handling manipulator arm 71. This allows the operator Y to shift the surgical tools 28 with precision. On the other hand, the controller 3 calculates the actual rotation amount of the actual surgical tool 28 by multiplying the rotation amount input by the operator Y by the scale factor of 1 or more, which causes the surgical tool 28 to move by an amplified movement amount of the handling manipulator arm 71. This allows the operator Y to promptly change the attitude of the surgical tool 28 in a large turn movement of the surgical tool 28 or the like by handling the handling manipulator arm 71 without large move of the entire body. This can improve the operability of the surgical system 100.

(Boundary Entry Restriction Process)

The controller 3 performs a boundary entry restriction process for restricting the attitudes of the tool manipulators 21 appearing in images captured by the camera probes 34 to a predetermined range with respect to the orientation of the image.

Figure 10:
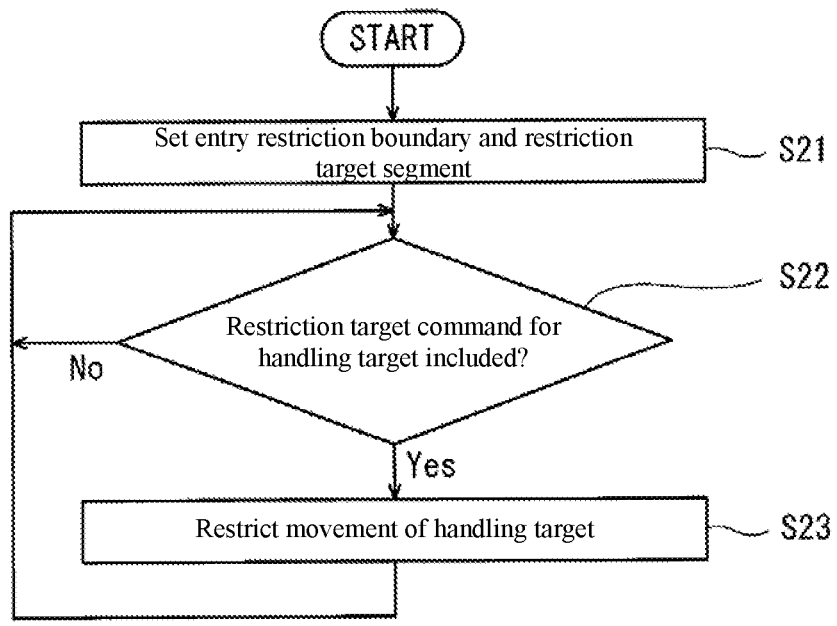
FIG. 10 is a flow chart showing an example of a boundary entry restriction process of the surgical system of FIG. 1.
Figure 11A:
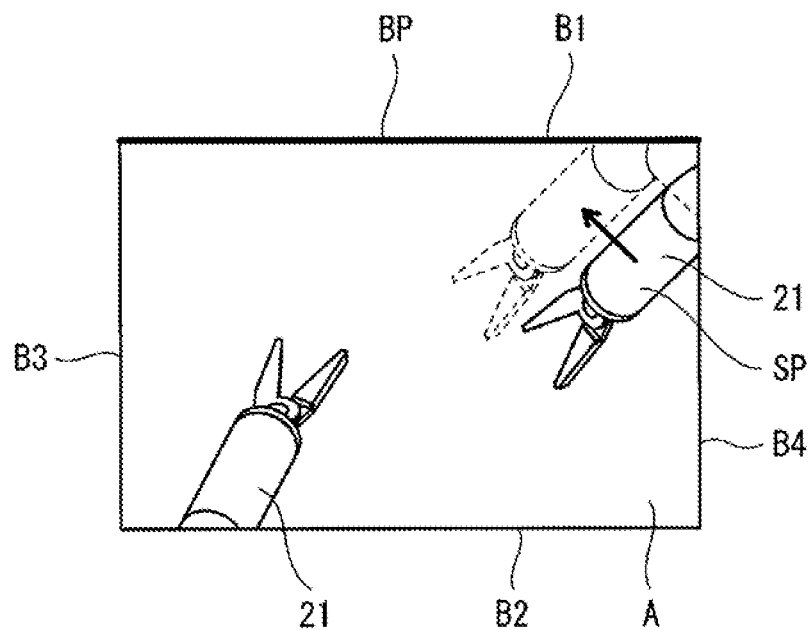
FIG. 11A is a diagram showing a movement example of the boundary entry restriction process of the surgical system of FIG. 1 and showing an image displayed on a display module.
Figure 11B:
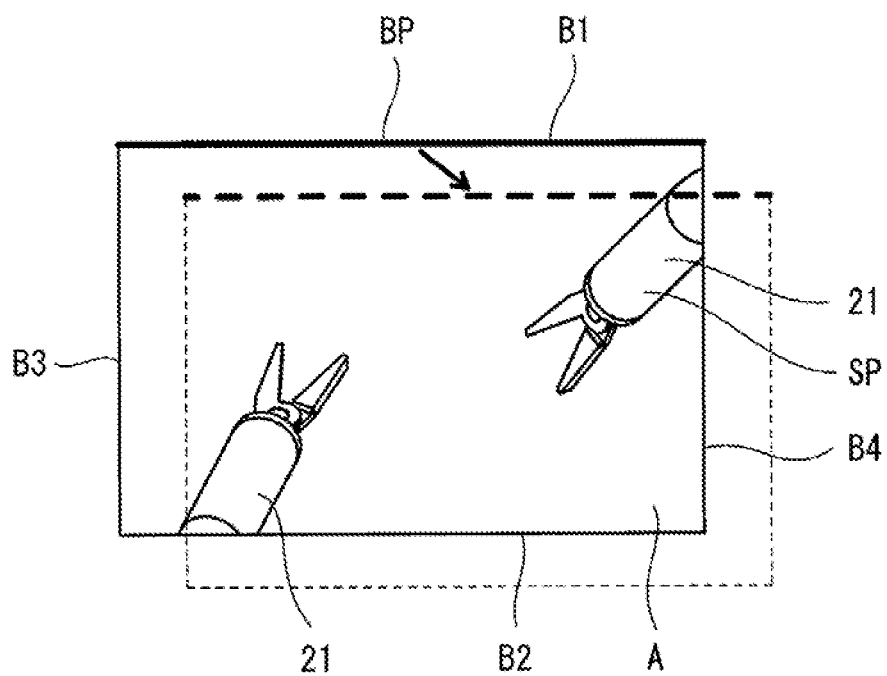
FIG. 11B is a diagram showing a movement example of the boundary entry restriction process of the surgical system of FIG. 1 and showing an image displayed on the display module.

FIG. 10 is a flow chart showing an example of the boundary entry restriction process of the surgical system 100. FIGS. 11A and 11B are diagrams showing movement examples in the boundary entry restriction process of the surgical system 100 and showing an image displayed on the display module 73.

First, as shown in FIG. 10, the controller 3 sets the upper boundary B1 of the imaging area A as an entry restriction boundary BP. The entry restriction boundary BP is a boundary on the upper side of the imaging area A and is displayed so as to be located on each upper side of the left and right display sections 73A and 73B. Note that the entry restriction boundary BP may extend to the left boundary B3 and the right boundary B4. The controller 3 sets restriction target segments SP (see FIG. 4) at the distal end side portions of the respective tool manipulators 21 (step S21).

Next, while moving a handling target, the controller 3 determines whether a movement command input by the operator Y includes a restriction target command to move the handling target so as to cause the restriction target segment SP of the tool manipulator 21 to enter the entry restriction boundary BP (step S22).

That is, when the handling target is the tool manipulator 21, the controller 3 determines whether the tool movement command includes a restriction target command to move the surgical tool 28 so as to cause the restriction target segment SP of the tool manipulator 21 to enter the entry restriction boundary BP, as shown in FIG. 11A. When the handling target is the endoscope manipulator 31, the controller 3 determines whether the endoscope movement command includes a second restriction target command to move the camera probes 34 so as to cause the restriction target segment SP to enter the entry restriction boundary BP crosswise, as shown in FIG. 11B. That is, it is determined whether the endoscope movement command includes a command to control the endoscope manipulator 31 such that the rotation of the endoscope manipulator 31 causes shifting of the position of the camera probes 34 and shifting of the restriction target segments SP, and as a result, the restriction target segment SP of the tool manipulator 21 enters the entry restriction boundary BP.

Upon determining that the restriction target command is included (Yes in step S22), the controller 3 sets zero to a component of the movement amount included in the movement command in the movement direction of the handling target that moves the restriction target segment SP into the entry restriction boundary BP crosswise. The controller 3 thus restricts the movement of the handling target in this direction. Alternatively, upon determining that no restriction target command is included (No in step S22), the controller 3 again performs the determination in step S22.

Accordingly, the extending directions of the tool manipulators 21 can be maintained equal to the extending directions of the arms of the operator Y in images captured by the camera probes 34, which can improve the operability of the surgical system 100.

Note that operational ranges may be set for the tool manipulators 21 and the endoscope manipulator 31 to keep the tool manipulators 21 from entering the boundary of the upper side of the imaging area A. Upon determining that the movement command includes a command that will cause deviation from the operational ranges, the controller 3 may restrict the movement toward the deviating direction. The restriction of movement may be performed mechanically by a mechanical stopper or the like, or may be performed by software using a soft limit or the like.

(Penetration Restriction Process)

Figure 12:
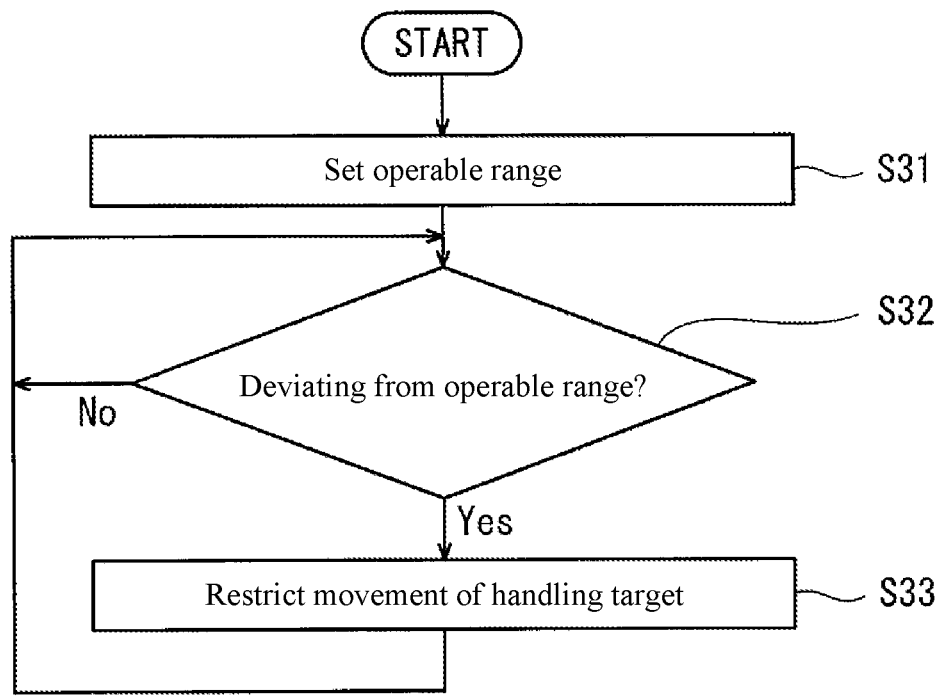
FIG. 12 is a flow chart showing an example of a penetration restriction process of the surgical system of FIG. 1.
Figure 13:
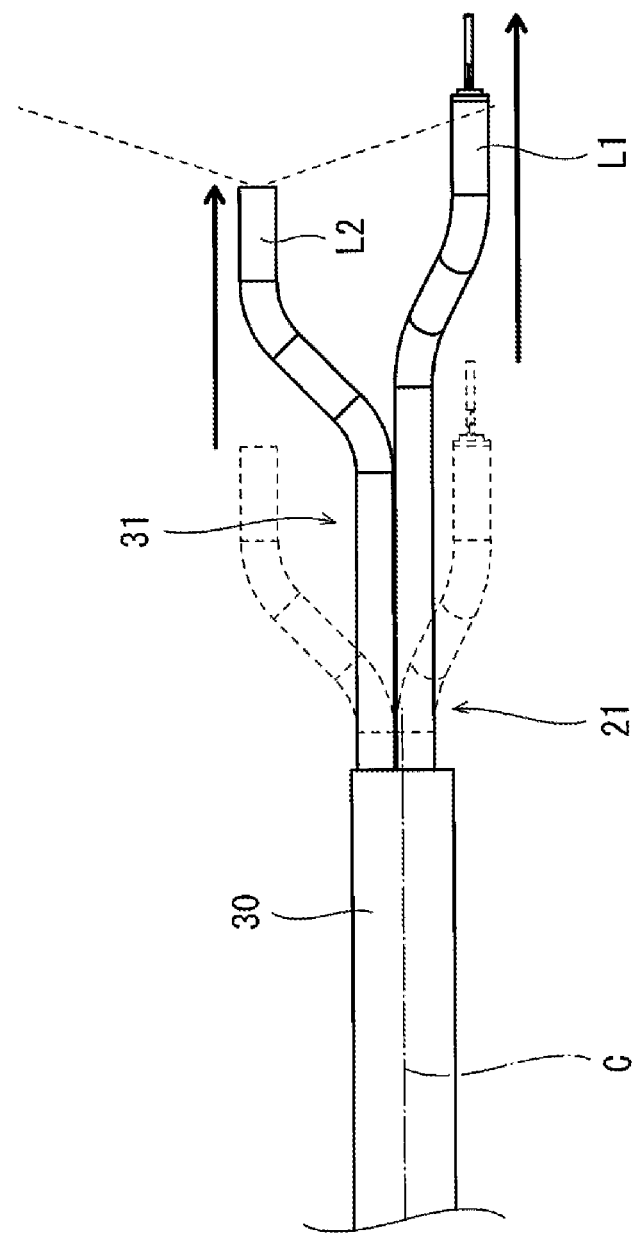
FIG. 13 is a diagram showing a movement example of the penetration restriction process of the surgical system of FIG. 1.

FIG. 12 is a flow chart showing an example of a penetration restriction process of the surgical system 100. FIG. 13 is a diagram showing a movement example in the penetration restriction process of the surgical system 100.

The controller 3 further performs a penetration restriction process for restricting translation of the tool manipulators 21 and the endoscope manipulator 31 in the extending direction of the central axis C.

First, the controller 3 sets an operable range of the tool manipulators 21 and the endoscope manipulator 31 (step S31). The operable range includes movable ranges of the tool manipulators 21 and the endoscope manipulator 31 in the extending direction of the central axis C. As shown in FIG. 13, the second penetration limit position L2 that is a distal-end-side limit position of the movable range of the endoscope manipulator 31 (second movable range) is set to be located more proximally than the first penetration limit positions L1 that are distal-side limit positions of the movable ranges of the tool manipulators 21 (first movable ranges), in the extending direction of the central axis C.

Next, while moving a handling target, the controller 3 determines whether the movement command input by the operator Y includes a command to move the handling target in a direction deviating from the operable range (step S32).

Upon determining that the movement command includes the command to move the handling target in the direction deviating from the operable range (Yes in step S32), the controller 3 sets zero to a component of the movement amount included in the movement command in the movement direction of the handling target that deviates from the operable range. The controller 3 thus restricts the movement of the handling target in this direction (Step S33). In this process, upon determining that the handling target has reached the first penetration limit position L1 that is the distal-side limit position of the movable range of the tool manipulator 21 (first movable range) in the extending direction of the central axis C, the controller 3 restricts the movement that shifts the handling target further distally. Alternatively, upon determining that the movement command does not include a command to move the handling target in the direction deviating from the operable range (No in step S32), the controller 3 again performs the determination in step S32.

The second penetration limit position L2 is set to be located more proximally than the first penetration limit positions L1 in the extending direction of the central axis C, which can effectively prevent losing sight of the surgical tool 28 due to its going out of view of the camera probes 34 for monitoring the movements of the surgical tools 28. This can improve the operability of the surgical system 100.

(Initial Movement Restriction Process)

The controller 3 further performs an initial movement restriction process for restricting movements of the wrists 27 of the tool manipulators 21 and the endoscope manipulator 31 until the wrists 27 pass the distal end of the entry guide 30. This process is performed when the surgical tools 28 and the camera probes 34 are introduced into the body cavity of the patient X.

First, the controller 3 determines whether the wrist 27 of a handling target is located more distally than the distal end of the entry guide 30 in the extending direction of the central axis C (the extending direction of the tool manipulators 21). That is, the controller 3 determines whether the wrist 27 is located more proximally than the distal end of the entry guide 30 or on the distal end of the entry guide 30 in the extending direction of the central axis C.

Upon determining that the proximal end of the wrist 27 of the handling target is not located more distally than the distal end of the entry guide 30 in the extending direction of the central axis C, the controller 3 sets zero to components of the movement amount included in the movement command in the directions other than the extending direction of the central axis C. The controller 3 thus restricts the movement of the handling target in the directions other than this one. The controller 3 repeatedly performs the determination until it determines that the wrist 27 of the handling target is located more distally than the distal end of the entry guide 30 in the extending direction of the central axis C. Upon determining that the wrist 27 of the handling target of the central axis C is located more distally than the distal end of the entry guide 30 in the extending direction of the central axis C, the controller 3 ends the process.

Accordingly, the tool manipulators 21 and the endoscope manipulator 31 can be rapidly introduced into the body cavity of the patient X, which can improve the operability of the surgical system 100.

(Body Wall Collision Prevention Process)

Figure 14:
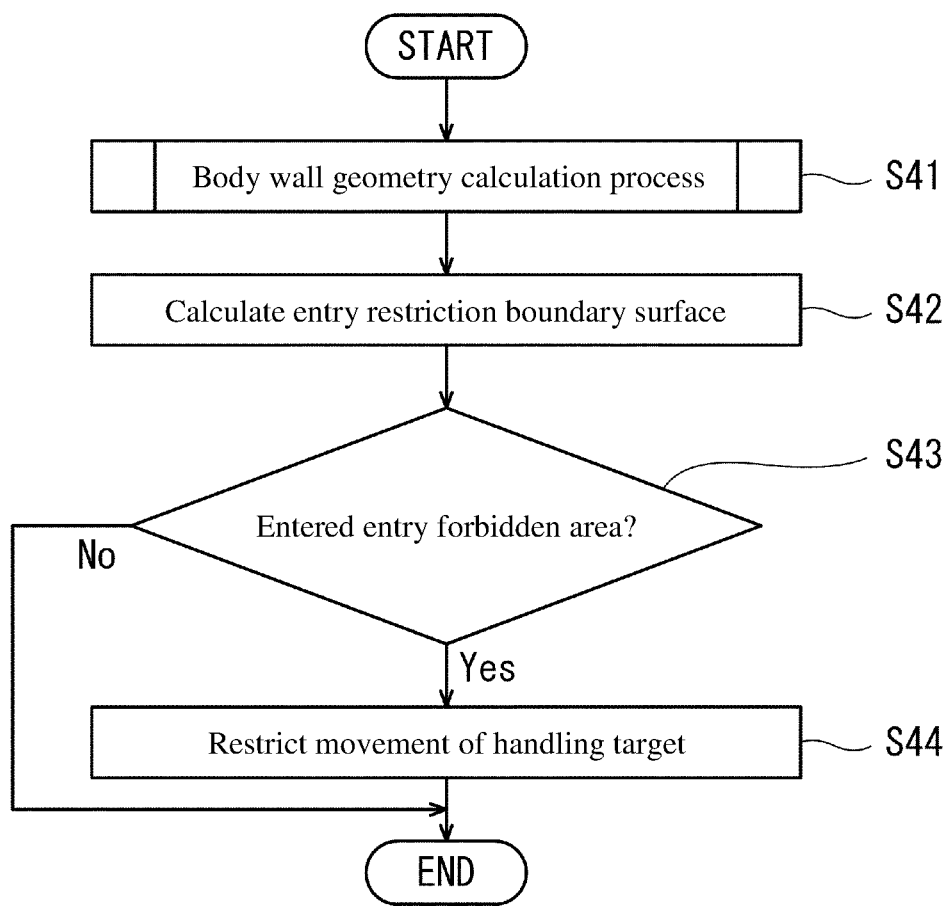
FIG. 14 is a flowchart showing an example of a body wall collision prevention process of the surgical system of FIG. 1.
Figure 15:
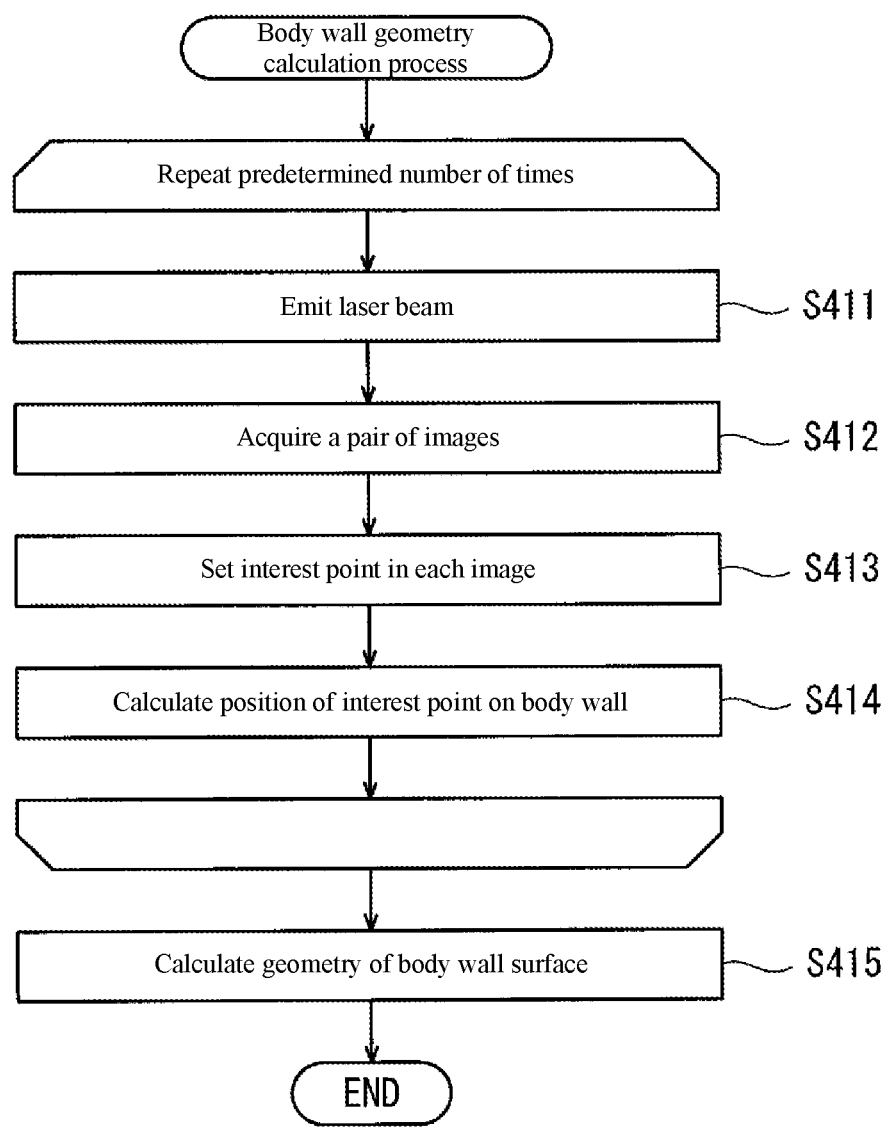
FIG. 15 is a flowchart showing an example of a body wall geometry calculation process in the body wall collision prevention process of the surgical system of FIG. 1.
Figure 16:
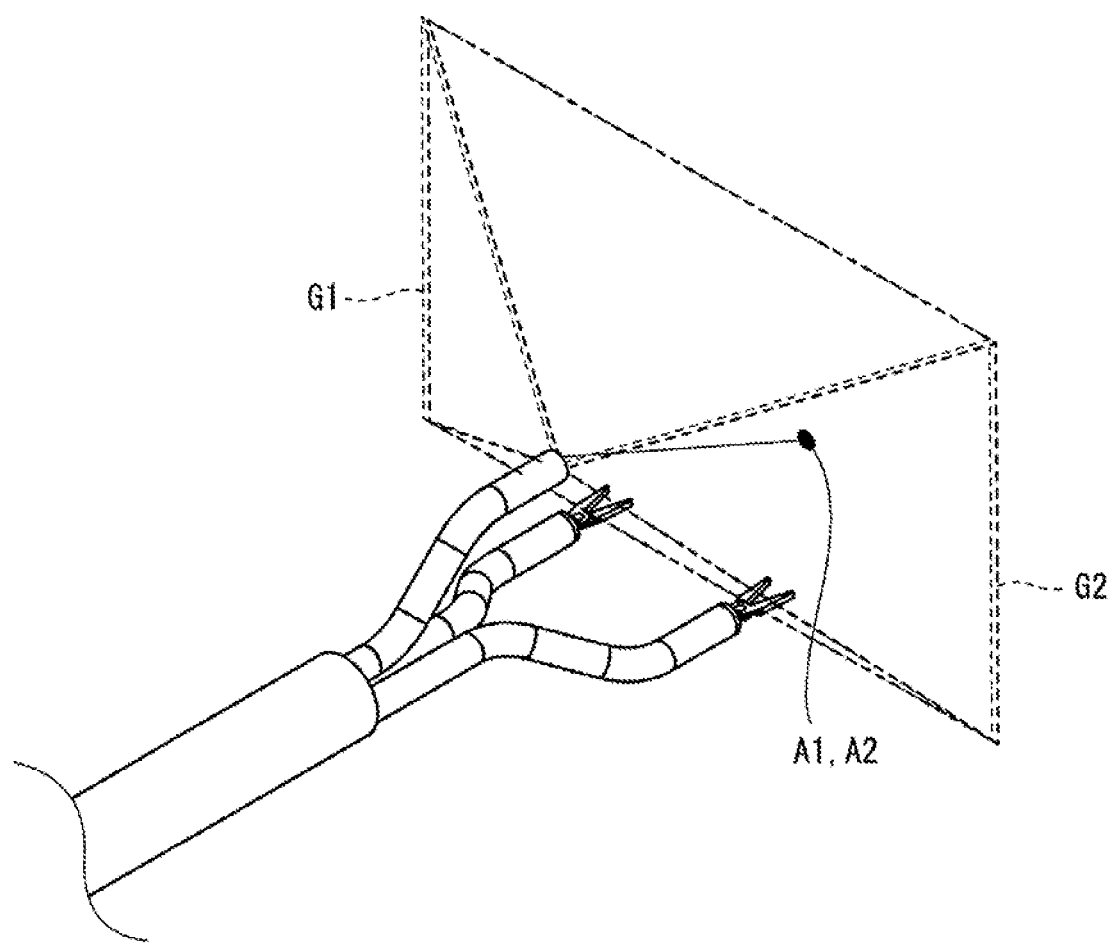
FIG. 16 is a diagram showing a movement example of the body wall collision prevention process of the surgical system of FIG. 1.
Figure 17:
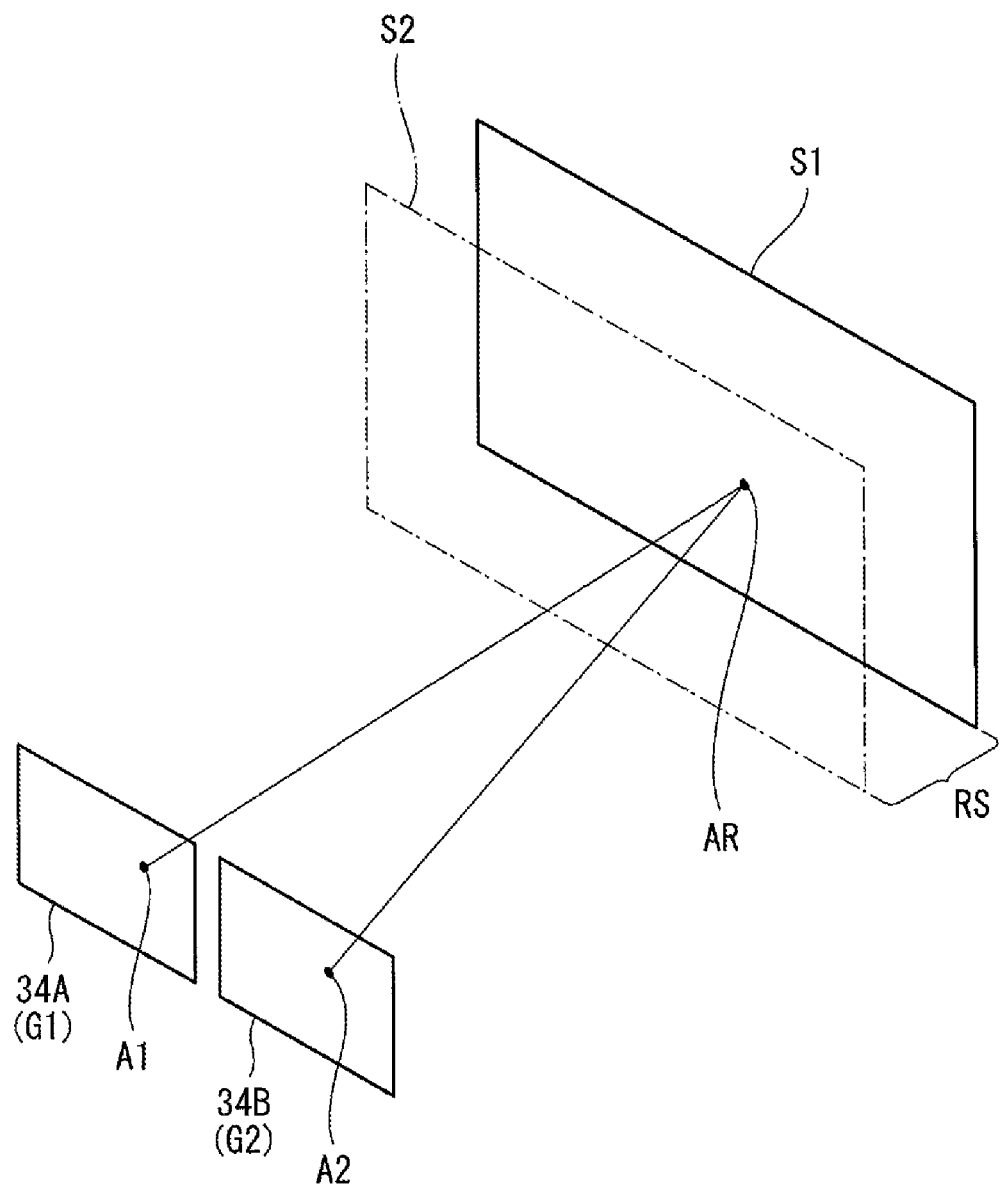
FIG. 17 is an illustrative diagram illustrating the body wall geometry calculation process of the surgical system of FIG. 1.

FIG. 14 is a flowchart showing an example of a body wall collision prevention process of the surgical system 100. FIG. 15 is a flowchart showing an example of a body wall geometry calculation process in the body wall collision prevention process of the surgical system 100. FIG. 16 is a diagram showing a movement example in the body wall collision prevention process of the surgical system 100. FIG. 17 is a diagram illustrating the body wall geometry calculation process in the body wall collision prevention process of the surgical system 100.

The controller 3 further performs a body wall collision prevention process repeatedly at predetermined time intervals for preventing collision of the tool manipulators 21 and the endoscope manipulator 31 with the body wall forming the body cavity of the patient X.

First, as shown in FIG. 14, the controller 3 calculates a three-dimensional map representing a three-dimensional geometry of the body wall as viewed from the body cavity of the patient X based on images acquired by the camera probes 34 (step S41).

The three-dimensional map is calculated by the following process shown in FIG. 15, for example. First, the controller 3 makes the laser pointer 36 of the endoscope manipulator 31 located in the body cavity of the patient X emit a laser beam (step S411). The emitting direction of the laser beam may be randomly selected. Next, the controller 3 acquires a pair of images G1 and G2 using the pair of camera probes 34 (step S412). Next, the controller 3 sets the irradiation portions of the laser beam recorded in the acquired pair of images G1 and G2 as interest points A1 and A2 of the respective images (step S413). As shown in FIG. 16, the difference in the positions of the camera probes 34A and 34B results in the differently recorded positions of the interest point A1 of the image G1 and the interest point A2 of the image G2. Note that the interest points in the pair of images may be set by pattern matching (details will be described later). As shown in FIG. 17, the controller 3 calculates the coordinates of the interest point AR on the body wall in the surgical-assist-robot-side three-dimensional orthogonal coordinate system based on the relative positional relationship between the interest point A1 of one image and the interest point A2 of the other image (step S414). The controller 3 repeats the above steps S411 to S414 a predetermined number of times. As described above, the emitting direction of the laser beam is randomly selected and the coordinate calculation process is repeatedly executed, resulting in the dispersedly set interest points. Next, the controller 3 calculates a surface passing through the coordinates of the dispersed interest points and then the geometry of the body wall forming the body cavity of the patient X (step S415). Accordingly, the pair of camera probes 34 derives information for detecting the geometry of the body wall forming the body cavity of the patient X (body wall geometry sensing section).

Next, the controller 3 calculates an entry restriction boundary surface S2 offset from the body wall surface S1 calculated in step S415 toward the body cavity side by a predetermined distance (step S42). An area between the entry restriction boundary surface S2 and the body wall surface S1 is an entry forbidden area.

Next, the controller 3 determines whether a handling target has moved past the entry restriction boundary surface S2 toward the body wall surface S1 side, i.e., whether the handling target has entered the entry forbidden area RS (step S43).

Upon determining that the handling target has entered the entry forbidden area RS (Yes in step S43), the controller 3 sets zero to a component of the movement amount included in the movement command in the movement direction of the handling target toward the body wall surface. The controller 3 thus restricts the movement of the handling target in this direction. The controller 3 makes the display module 73 display information for notifying that the handling target has entered the entry forbidden area RS. Note that upon determining that the handling target has not entered the entry forbidden area RS (No in step S43), the controller 3 skips step S44.

This can prevent collision of the tool manipulators 21 and the endoscope manipulator 31 as handling targets with the body wall.

(Position Change Cancellation Process)

Figure 18:
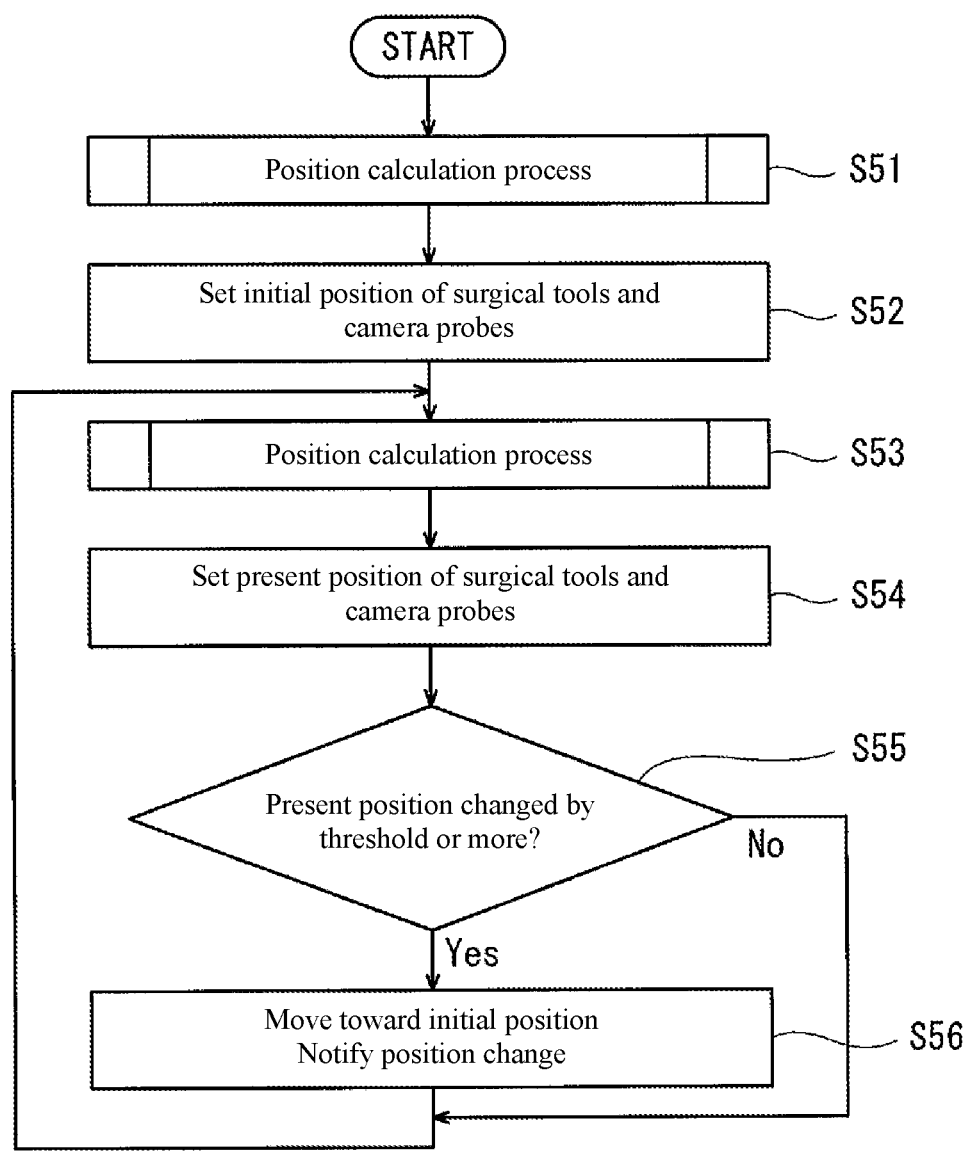
FIG. 18 is a flow chart showing an example of a position change cancellation process of the surgical system of FIG. 1.
Figure 19:
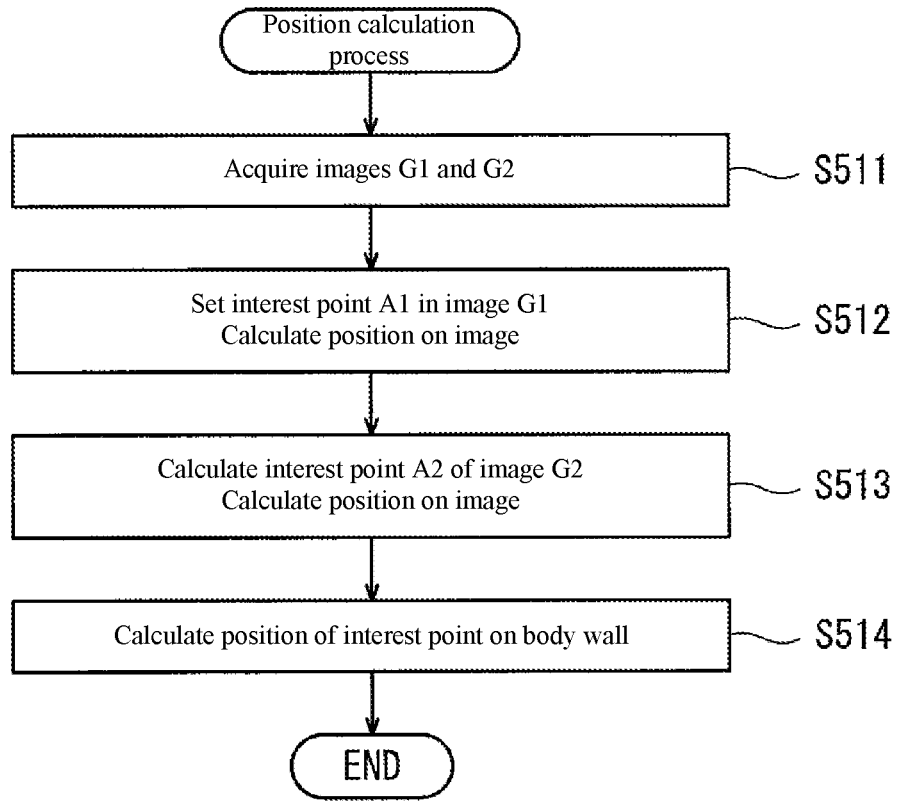
FIG. 19 is a flow chart showing an example of a position calculation process in the position change cancellation process of the surgical system of FIG. 1.

FIG. 18 is a flow chart showing an example of a position change cancellation process of the surgical system 100. FIG. 19 is a flow chart showing an example of a position calculation process in the position change cancellation process of the surgical system 100.

When unexpected movement of the entry guide 30, for example, due to attitude change of the patient X is followed by shifting of the surgical tools 28 and the camera probes 34, the controller 3 further performs a position change cancellation process for moving the surgical tools 28 and the camera probes 34 in a direction such that the change in the position of the surgical tools 28 and the camera probes 34 is canceled.

First, as shown in FIG. 18, upon determining that no endoscope movement command has been input for a predetermined time, the controller 3 calculates the position of an interest point AR set on the body wall forming the body cavity of the patient X (see FIG. 7) and calculates the position of the surgical tools 28 and the camera probes 34 based on the position of this interest point AR. The calculated position of the surgical tools 28 and the camera probes 34 is set as an initial position (step S51). The interest point AR is set based on the images acquired by the camera probes 34.

The position of the interest point AR is calculated by pattern matching as follows. First, the controller 3 acquires a pair of images G1 and G2 using the pair of camera probes 34 (step S511). Next, the controller 3 sets an interest point A1 in one image G1 of the acquired pair of images and calculates the position of the interest point A1 on the image (step S512). Next, a place on the body wall recorded in the other image G2, the place being identical to the place of the interest point A1, is decided by pattern matching between the pair of images G1 and G2. The decided place is set as the interest point A2. The controller 3 then calculates the position of the interest point A2 on the image G2 (step S513). The controller 3 then calculates the interest point AR on the body wall corresponding to the interest point A1 and the interest point A2 based on the relative positional relationship between the interest points A1 and A2 (step 514). The coordinates calculation can be performed by the same method as the method in the body wall geometry calculation process described above in the body wall collision prevention process. Note that subsequent processing stops upon input of an endoscope movement command.

Next, after a predetermined sampling period, the controller 3 calculates the position of the interest point AR and then the position of the surgical tools 28 and the camera probes 34 based on the position of this interest point AR (step S53). The calculated position of the surgical tools 28 and the camera probes 34 is set as a present position (step S54).

Next, the controller 3 compares the initial position with the present position and determines whether the present position has changed by a predetermined threshold or more with respect to the initial position (step S55).

Upon determining that the present position has changed by the predetermined threshold or more with respect to the initial position (Yes in step S55), the controller 3 moves the surgical tools 28 and the camera probes 34 toward the initial position. The controller 3 also makes the display section display information for notifying that the present position has changed. Then, the controller 3 again performs step S53 until an endoscope movement command is input.

Accordingly, the surgical tools 28 and the camera probes 34 automatically return to the initial position even when the position of the surgical tools 28 and the camera probes 34 has changed due to unexpected change of the position of the entry guide 30, which can alleviate adverse effect on the operability for the operator and improve the operability of the surgical system 100. In addition, the operator Y can recognize that the position of the entry guide 30 has changed.

Second Embodiment

Hereinafter, a configuration and movement of a second embodiment will be described focusing on differences from the first embodiment.

Figure 20:
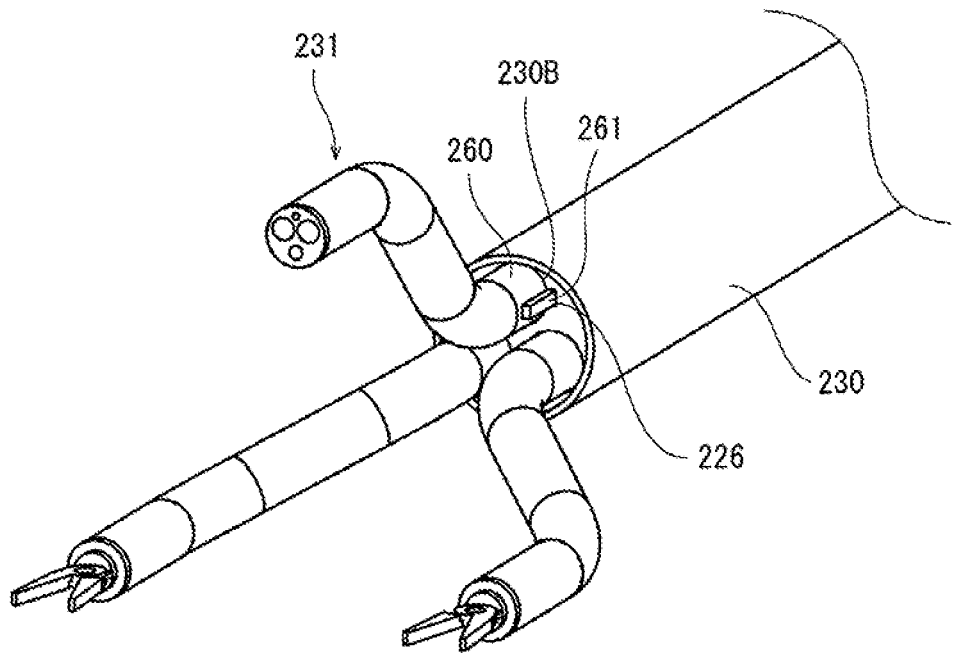
FIG. 20 is a perspective view showing a distal end of a surgical assist robot of a surgical system according to a second embodiment.

FIG. 20 is a perspective view showing a distal end of a surgical assist robot of a surgical system according to a second embodiment.

In the first embodiment described above, the endoscope manipulator 31 is rotatable in the circumferential direction around the central axis of the endoscope insertion hole 30B of the entry guide 30.

On the other hand, in the present embodiment, an endoscope manipulator 231 has a rotation restriction structure that restricts rotation of the endoscope manipulator 231 in the circumferential direction around the central axis of an endoscope insertion hole 230B of an entry guide 230.

The rotation restriction structure includes, for example, a projection 261 sticking out in a radial direction of a shaft 260, and a groove 226 that is formed on the inner periphery of the endoscope insertion hole 230B and engages with the projection 261. The projection 261 extends along the shaft 260. The endoscope manipulator 231 has no wrist joint 63. Furthermore, a first sub drive unit 22A of a surgical assembly 20B has no rotation driver assembly 41 and a second sub drive unit 22B is attached to a translation driver assembly 42.

In this manner, rotation of the endoscope manipulator 231 is restricted in the circumferential direction around the central axis of the endoscope insertion hole 230B of the entry guide 230 with respect to the entry guide 230, which makes it possible to maintain the orientation of an endoscope image with respect to the entry guide 230 and tool manipulators 21 and thus for the operator Y to easily recognize the positions of the surgical tools 28. This can improve the operability of the surgical system 100.

In addition, as described in detail in the first embodiment, the tool manipulators 21 are rotatable in the circumferential direction around the central axis of the tool manipulator insertion hole 230A of the entry guide 230 with respect to the entry guide 230, which can improve the operability of the surgical system 200.

Furthermore, as described in detail in the first embodiment, a support frame 14 is rotatable in the circumferential direction around the central axis of the entry guide 230 (i.e., the central axis C), which makes it possible to change the attitude of the distal end of the surgical assist robot 1 with the orientation of the endoscope image with respect to the entry guide 230 and the tool manipulators 21 maintained. This can improve the operability of the surgical system 200.

Third Embodiment

Hereinafter, a configuration and movement of a third embodiment will be described focusing on differences from the first embodiment.

In the above embodiment, the surgical system 100 restricts movements of the wrists 27 by the initial movement restriction process until the wrists 27 of the tool manipulators 21 and the endoscope manipulator 31 pass the distal end of the entry guide 30. The present invention is, however, not limited to this, and instead, a brake may be provided such that its actuation restricts rotation of a driven pulley 25a or a drive pulley 44a corresponding to a wrist 27 and its deactuation allows the rotation of the driven pulley 25a or the drive pulley 44a.

From the above description, several improvements and other embodiments of the present invention will be apparent to those skilled in the art. Accordingly, the above description is to be construed as illustrative only and is provided for the purpose of teaching those skilled in the art the best mode of carrying out the present invention. It is possible to substantially change the details of its structure and/or function without departing from the spirit of the present invention.

What is claimed is:

1. A surgical system comprising:
   a tool manipulator including a tool manipulator arm that has a tool manipulator arm distal end and a tool manipulator arm proximal end and is configured to perform translational motion and rotational motion of the tool manipulator arm distal end with respect to the tool manipulator arm proximal end, and a surgical tool provided to the tool manipulator arm distal end;
   a console including a handling tool configured to receive a tool movement command of a surgeon for the surgical tool, the tool movement command including a translation amount of the translational motion and a rotation amount of the rotational motion for the surgical tool; and
   a controller configured to control the tool manipulator, wherein
   the controller is configured to calculate an actual translation amount by multiplying the translation amount for the surgical tool received by the handling tool by a predetermined translation scale factor and move the surgical tool in accordance with the actual translation amount, and to calculate an actual rotation amount by multiplying the rotation amount for the surgical tool received by the handling tool by a predetermined rotation scale factor and move the surgical tool in accordance with the actual rotation amount, and
   the predetermined translation scale factor and the predetermined rotation scale factor are different values.

2. The surgical system according to claim 1, wherein the predetermined rotation scale factor is a value larger than the predetermined translation scale factor.

3. The surgical system according to claim 1, comprising an endoscope including a camera probe configured to capture an image of an imaging area surrounded by a boundary including a preset entry restriction boundary, wherein
   the console includes a display module having a display area on which the image captured by the camera probe is displayed and the display module is configured to arrange the preset entry restriction boundary on an upper side of the display area to display the image captured by the camera probe, and
   the controller is configured to restrict, upon determining that the tool movement command includes a command to move the surgical tool so as to move a restriction target segment set at a distal end side of the tool manipulator into the preset entry restriction boundary, movement of the surgical tool in a movement direction of the surgical tool that moves the restriction target segment into the preset entry restriction boundary.

4. The surgical system according to claim 3, wherein
   the endoscope includes an endoscope manipulator arm having an endoscope manipulator arm distal end and an endoscope manipulator arm proximal end and configured to perform translational motion and rotational motion of the endoscope manipulator arm distal end with respect to the endoscope manipulator arm proximal end and the camera probe is provided to the endoscope manipulator arm distal end,
   the handling tool is configured to receive an endoscope manipulator movement command of a surgeon for the camera probe, the endoscope manipulator movement command including a translation amount of the translational motion and a rotation amount of the rotational motion for the camera probe, and
   the controller is configured to restrict, upon determining that the endoscope manipulator movement command includes a command to move the camera probe so as to move the restriction target segment into the preset entry restriction boundary, movement of the camera probe in a movement direction of the camera probe that moves the restriction target segment into the preset entry restriction boundary.

5. The surgical system according to claim 1, comprising:
   an endoscope including an endoscope manipulator arm that has an endoscope manipulator arm distal end and an endoscope manipulator arm proximal end and is configured to perform translational motion and rotational motion of the endoscope manipulator arm distal end with respect to the endoscope manipulator arm proximal end, and a camera probe provided to the endoscope manipulator arm distal end of the endoscope manipulator arm; and
   an entry guide having an endoscope insertion hole through which the endoscope manipulator arm is inserted, wherein
   the console includes a display module having a display area on which an image captured by the camera probe is displayed in a predetermined orientation, and
   the entry guide has a rotation restriction structure configured to restrict rotation of the endoscope manipulator arm in a circumferential direction around a central axis of the endoscope insertion hole.

6. The surgical system according to claim 5, wherein
   the entry guide has a tool manipulator insertion hole through which the tool manipulator arm is inserted, and the tool manipulator arm is rotatable in a circumferential direction around a central axis of the tool manipulator insertion hole.

7. The surgical system according to claim 5, comprising an entry guide support structure supporting the entry guide rotatably in a circumferential direction around a central axis of the entry guide.

8. The surgical system according to claim 1, comprising:
an endoscope including an endoscope manipulator arm that has an endoscope manipulator arm distal end and an endoscope manipulator arm proximal end and is configured to perform translational motion and rotational motion of the endoscope manipulator arm distal end with respect to the endoscope manipulator arm proximal end, and a camera probe provided to the endoscope manipulator arm distal end; and
an entry guide having a first insertion hole and a second insertion hole, wherein the tool manipulator arm is inserted through the first insertion hole and the endoscope manipulator arm is inserted through the second insertion hole,
wherein the controller is configured to shift the tool manipulator arm in an extending direction of the first insertion hole with respect to the entry guide within a predetermined first movement range, and to shift the endoscope manipulator arm in an extending direction of the second insertion hole with respect to the entry guide within a predetermined second movement range, and
a distal-end-side limit of the predetermined second movement range is located more proximally than a distal-end-side limit of the predetermined first movement range.

9. The surgical system according to claim 1, comprising an entry guide having an entry guide distal end and an entry guide proximal end and having an insertion hole through which the tool manipulator arm and the surgical tool are inserted, wherein
the tool manipulator arm includes a wrist structure that is provided at a proximal side of the surgical tool and performs at least a part of the translational motion and the rotational motion of the tool manipulator arm,
the tool manipulator has a brake configured to restrict movement of the wrist structure by actuation and allow the movement of the wrist structure by deactuation, and
the controller is configured to actuate the brake when the wrist structure is located more proximally than the entry guide distal end or on the entry guide distal end in an extending direction of the tool manipulator arm.

10. The surgical system according to claim 1, comprising an entry guide having an entry guide distal end and an entry guide proximal end and having a tool manipulator insertion hole through which the tool manipulator arm and the surgical tool are inserted, wherein
the tool manipulator arm has a wrist structure that is provided at a proximal side of the surgical tool and performs at least a part of the translational motion and the rotational motion of the tool manipulator arm by movement of the wrist structure, and
the controller is configured to invalidate a movement command for the wrist structure included in the tool movement command when the wrist structure is located more proximally than the entry guide distal end of the entry guide or on the entry guide distal end of the entry guide in an extending direction of the tool manipulator arm.

11. The surgical system according to claim 1, comprising:
an endoscope including a body wall geometry sensing section configured to derive information for detecting a geometry of a body wall forming a body cavity of a patient; and
a notification section configured to notify the surgeon of information, wherein the controller is configured to
calculate the geometry of the body wall based on the information derived by the body wall geometry sensing section,
set an entry forbidden area based on the calculated geometry of the body wall, and
repeatedly determine whether the tool manipulator has entered the entry forbidden area and control, upon determining that the tool manipulator has entered the entry forbidden area, the notification section to notify the surgeon that the tool manipulator has entered the entry forbidden area.

12. The surgical system according to claim 11, wherein
the body wall geometry sensing section is a pair of camera probes provided at an endoscope distal end of the endoscope and arranged with predetermined spacing, and
the controller is configured to
dispersedly set a plurality of interest points on the body wall recorded in images captured by the pair of camera probes,
calculate, for each of the interest points, three dimensional coordinates of the interest point with respect to a predetermined reference point, based on a relative positional relationship between a position of a first interest point in a first image captured by one of the camera probes and a position of a second interest point in a second image captured by the other of the camera probes simultaneously with the first image, and
calculate the geometry of the body wall based on the calculated three-dimensional coordinates of the plurality of interest points.

13. The surgical system according to claim 12, wherein
the endoscope includes a laser pointer provided at the endoscope distal end and configured to emit a laser beam, and
the controller is configured to set a first irradiation portions of the laser beam recorded in the first image and a second irradiation portion of the laser beam recorded in the second image as the first interest point in the first image and the second interest point of the second image, respectively.

14. The surgical system according to claim 12, wherein the controller is configured to:
set the first interest point in the first image in which the body wall is recorded,
calculate a second place in the second image in which the body wall is recorded, the second place being identical to a first place of the first interest point in the first image and calculated by pattern matching between the first image and the second image, and
set the second place as the second interest point in the second image.

15. The surgical system according to claim 1, comprising:
an endoscope including a pair of camera probes arranged with predetermined spacing; and
a notification section configured to notify the surgeon of information, wherein
the controller is configured to
set an initial interest point on a body wall forming a body cavity of a patient recorded in images captured by the camera probes, calculate an initial position of the pair of camera probes with respect to the initial interest point, based on a position of a first initial interest point in a first image captured by one of the pair of camera probes and a position of a second initial interest point in a second image captured by the other of the pair of camera probes, calculate a present position of the pair of camera probes with respect to a present interest point, based on a position of a first present interest point in the first image and a position of a second present interest point in the second image, and determine whether the present position has changed by a predetermined threshold or more with respect to the initial position, and control, upon determining that the present position has changed by the predetermined threshold or more with respect to the initial position, wherein the notification section notifies that the present position has changed.

16. The surgical system according to claim 15, wherein the endoscope includes an endoscope manipulator arm having an endoscope manipulator arm distal end and an endoscope manipulator arm proximal end and configured to perform translational motion and rotational motion of the endoscope manipulator arm distal end with respect to the endoscope manipulator arm proximal end and the pair of camera probes are provided to the endoscope manipulator arm distal end of the endoscope manipulator arm, and the controller is configured to move the pair of camera probes toward the initial position upon determining that the present position has changed by a predetermined threshold or more with respect to the initial position.

17. A method of controlling a surgical system, the surgical system comprising:

a tool manipulator including a tool manipulator arm having a tool manipulator arm distal end and a tool manipulator arm proximal end and configured to perform a translational motion and a rotational motion of the tool manipulator arm distal end with respect to the tool manipulator arm proximal end, and a surgical tool linked to the tool manipulator arm distal end;

a console having a handling tool configured to receive a tool movement command of a surgeon for the surgical tool, the tool movement command including a translation amount of the translational motion and a rotation amount of the rotational motion for the surgical tool; and a controller configured to control the tool manipulator, the method comprising:

calculating, by the controller, an actual translation amount by multiplying the translation amount for the surgical tool received by the handling tool by a predetermined translation scale factor;

moving, by the controller, the surgical tool in accordance with the actual translation amount;

calculating, by the controller, an actual rotation amount by multiplying the rotation amount for the surgical tool received by the handling tool by a predetermined rotation scale factor that is a value different from the predetermined translation scale factor; and moving, by the controller, the surgical tool in accordance with the actual rotation amount.

18. The method of controlling the surgical system according to claim 17, wherein the predetermined rotation scale factor is a value larger than the predetermined translation scale factor.

19. The method of controlling the surgical system according to claim 17, the surgical system comprising an endoscope having a camera probe configured to capture an image of an imaging area surrounded by a boundary including a preset entry restriction boundary, wherein the console has a display module having a display area on which the image captured by the camera probe is displayed and the display module is configured to arrange the preset entry restriction boundary on an upper side of the display area to display the image captured by the camera probe; and the controller restricts, upon determining that the tool movement command includes a command to move the surgical tool so as to move a restriction target segment set at the tool manipulator arm distal end of the tool manipulator into the preset entry restriction boundary, movement of the surgical tool in a movement direction of the surgical tool that moves the restriction target segment into the preset entry restriction boundary.

20. The method of controlling the surgical system according to claim 17, the surgical system comprising:

an endoscope including an endoscope manipulator arm having an endoscope manipulator arm distal end and an endoscope manipulator arm proximal end and configured to perform a second translational motion and a second rotational motion of the endoscope manipulator arm distal end with respect to the endoscope manipulator arm proximal end, and a camera probe linked to the endoscope manipulator arm distal end; and an entry guide having an endoscope insertion hole through which the endoscope manipulator arm is inserted, wherein the console has a display module having a display area on which an image captured by the camera probe is displayed in a predetermined orientation, and the entry guide has a rotation restriction structure configured to restrict rotation of the endoscope manipulator arm in a circumferential direction around a central axis of the endoscope insertion hole.

\* \* \* \* \*